United States Patent [19]

Sekiya et al.

[11] Patent Number: 5,202,351
[45] Date of Patent: Apr. 13, 1993

[54] 1-PHENYLALKYL-3-PHENYLUREA DERIVATIVE

[75] Inventors: Tetsuo Sekiya, Yokohama; Shinya Inoue, Tokyo; Chiaki Hyodo, Machida; Hiromi Okushima, Kawasaki; Kohei Umezu, Yokohama; Kazuo Suzuki, Machida, all of Japan

[73] Assignee: Mitsubishi Kasei Corporation, Tokyo, Japan

[21] Appl. No.: 643,983

[22] Filed: Jan. 22, 1991

[30] Foreign Application Priority Data

Jan. 22, 1990 [JP] Japan ................................ 2-12235
Feb. 8, 1990 [JP] Japan ................................ 2-28768

[51] Int. Cl.$^5$ .............................................. C07D 317/44
[52] U.S. Cl. .............................................. 514/450; 514/452; 514/464; 514/465; 549/350; 549/365; 549/366; 549/434; 549/441
[58] Field of Search ............. 549/444, 441, 434, 350, 549/365, 366; 564/48, 56; 514/450, 452, 464, 465

[56] References Cited

U.S. PATENT DOCUMENTS

| | | | |
|---|---|---|---|
| 2,485,600 | 11/1949 | Hedenburg | 549/434 |
| 4,102,673 | 7/1978 | Buntin | 564/48 |
| 4,127,673 | 11/1978 | Yamada et al. | 564/48 |
| 4,405,644 | 9/1983 | Kabbe et al. | 564/48 |
| 4,937,360 | 6/1990 | Liu et al. | 549/441 |

FOREIGN PATENT DOCUMENTS

| | | |
|---|---|---|
| 0384320 | 4/1979 | European Pat. Off. . |
| 0335375 | 3/1983 | European Pat. Off. . |
| 6183 | 7/1981 | France . |

OTHER PUBLICATIONS

Shin-Jikken Kagaku Koza 14, "Synthesis and Reaction of Organic Compound (II)", p. 921.
Shin-Jikken Kagaku Koza 14, "Synthesis and Reaction of Organic Compound (III)", pp. 1332, 1447, 1490, 1503.

Primary Examiner—C. Warren Ivy
Assistant Examiner—Raymond Covington
Attorney, Agent, or Firm—Foley & Lardner

[57] ABSTRACT

A novel 1-phenylalkyl-3-phenylurea derivative represented by the following formula (I):

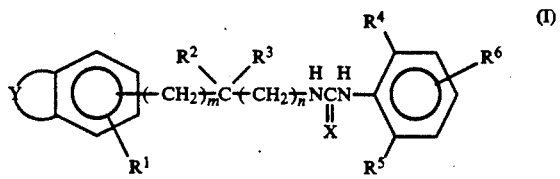

wherein $R^1$ and $R^5$ represent independently hydrogen, $C_1$–$C_6$ alkyl, $C_1$–$C_5$ alkoxyl or halo; $R^2$ represents hydrogen or $C_1$–$C_{15}$ alkyl; $R^3$ represents $C_1$–$C_{15}$ alkyl or $R^3$ represents together with $R^2$ $C_2$–$C_9$ alkylene; $R^4$ and $R^5$ represent independently $C_1$–$C_5$ alkyl, $C_1$–$C_5$ alkoxyl or halo; X represents oxygen or sulfur; Y represents —O—$(CH_2)_l$—O— wherein l is an integer of 1 to 3 or —$(CH_2)_p$— wherein p is an integer of 3 to 5; m is 0 or an integer of 1 to 5; and n is 0 or an integer of 1 to 3, is provided. The 1-phenylalkyl-3-phenylurea derivative (I) have the action of reducing cholesterol in blood by ACAT inhibition, and therefore, useful for treating hyperlipemia and atherosclerosis.

16 Claims, No Drawings

1-PHENYLALKYL-3-PHENYLUREA DERIVATIVE

BACKGROUND OF THE INVENTION

The present invention relates to 1-phenylalkyl-3-phenylurea derivatives and 1-phenylalkyl-3-phenylthiourea derivatives which are potent in reducing a lipid level in blood and, therefore, useful as therapeutical medicines for hyperlipemia and atherosclerosis.

Heretofore, it has been considered that hyperlipemia caused by metabolic disorder of lipids results in arteriosclerosis and is one of the major dangerous factors causing ischemic heart disease or cerebral embolism.

Recently, it was revealed that an enzyme, acyl-CoA: cholesterol acyltransferase (ACAT) acts an important role at lipid metabolism, especially cholesterol metabolism. It is expected that compounds having an inhibitory activity of the enzyme, ACAT, actually inhibit the absorption of cholesterol at intestine, reduce the level of cholesterol in blood, and inhibit the deposition of cholesterol on arterial wall. Therefore, compounds having an inhibitory activity of ACAT, are useful as therapeutical medicines for atherosclerosis as well as hyperlipemia.

As examples for such compounds having an inhibitory activity of ACAT, 1-phenylalkyl-3-phenylurea derivatives are disclosed in Japanese Patent Application Laid-Open (KOKAI) No.316761/88, No.93569/89, No.6455/90, No. 6456/90, No. 6457/90, No. 258756/90, and 275848/90.

The compound according to the present invention is novel and has a high inhibitory activity of ACAT and a high cholesterol reducing action in blood.

SUMMARY OF THE INVENTION

As a result of further researches for the compounds showing even higher lipid reducing action than the hitherto proposed compounds such as mentioned above, the present inventors have found the novel and useful urea derivatives and attained the present invention based on the finding.

Specifically, the present invention provides a 1-phenylalkyl-3-phenylurea derivative represented by the following formula (I):

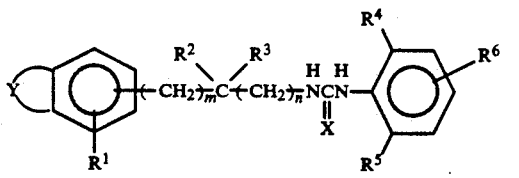

wherein $R^1$ and $R^6$ represent independently hydrogen $C_1$–$C_5$ alkyl, $C_1$–$C_5$ alkoxyl or halo; $R^2$ represents hydrogen or $C_1$–$C_{15}$ alkyl; $R^3$ represents $C_1$–$C_{15}$ alkyl or $R^3$ represents together with $R^2$ $C_2$–$C_9$ alkylene; $R^4$ and $R^5$ represent independently $C_1$–$C_5$ alkyl, $C_1$–$C_5$ alkoxyl or halo; X represents oxygen or sulfur; Y represents —O—$(CH_2)l$—O— wherein l is an integer of 1 to 3 or —$(CH_2)_p$— wherein p is an integer of 3 to 5; m is an integer of 0 to 5; and n is an integer of 0 to 3.

DETAILED DESCRIPTION OF THE INVENTION

The present invention is described in detail below.

The compounds according to the present invention are represented by the above-shown general formula (I). As the $C_1$–$C_5$ alkyl represented by $R^1$, $R^4$, $R^5$ and $R^6$ in the above formula, there can be mentioned methyl, ethyl, n-propyl, isopropyl, n-butyl, isobutyl, sec-butyl, tert-butyl, n-pentyl, sec-pentyl and neopentyl. As the $C_1$–$C_5$ alkoxyl represented by $R^1$, $R^4$, $R^5$ and $R^6$, there can be mentioned methoxyl, ethoxyl, n-propoxyl, isopropoxyl, n-butoxyl, sec-butoxyl, tert-butoxyl, n-pentoxyl, sec-pentoxyl and neopentoxyl. As the halo represented by $R^1$, $R^4$, $R^5$ and $R^6$, there can be mentioned fluorine, chlorine, bromine and iodine.

As the $C_1$–$C_{15}$ alkyl represented by $R^2$ and $R^3$ in the above formula (I), there can be cited methyl, ethyl, n-propyl, isopropyl, n-butyl, isobutyl, n-pentyl, isopentyl, neopentyl, n-hexyl, isohexyl, n-heptyl, n-octyl, n-nonyl, n-decyl, n-undecyl, n-dodecyl, n-tridecyl, n-tetradecyl and n-pentadecyl.

Examples of the compounds of this invention represented by the formula (I) are shown in Table 8 to 19. Some of the compounds of this invention have an asymmetric carbon in their molecule, and racemates, optical isomers and diastereomers may be also included in the present invention.

In the present invention, is preferred a compound wherein $R^1$ represents hydrogen, methyl, methoxyl or chlorine; $R^2$ represents hydro or $C_1$–$C_5$ alkyl; $R^3$ represents $C_2$–$C_8$ alkyl or represents together with $R^2$ $C_3$–$C_5$ alkylene; $R^4$ and $R^5$ represent independently $C_1$–$C_5$ alkyl, $C_1$–$C_5$ alkoxyl or halo; $R^6$ represents hydrogen, methyl, methoxyl or chlorine; m represents 0 or an integer of 1 to 3; and n represents 0, 1 or 2. More preferred is a compound wherein each of $R^1$ and $R^6$; represents hydrogen; $R^2$ represents hydrogen or $C_1$–$C_3$ alkyl; $R^3$ represents $C_2$–$C_8$ alkyl; each of $R^4$ and $R^5$ represents isopropyl; X represents oxygen; m represents 0 and n represents 1.

The processes for preparing the compounds of this invention are described below.

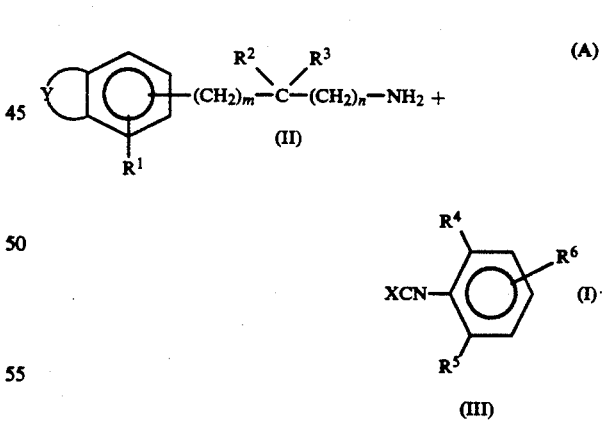

(wherein $R^1$, $R^2$, $R^3$, $R^4$, $R^5$, $R^6$, X, Y, m and n are as defined above).

A phenylalkylamine derivative (II) and a phenyl isocyanate derivative (III) (or a phenyl isothiocyanate derivative) are condensed at a temperature in the range of 0° C. to 150° C. in a solvent which does not participate in the reaction, such as benzene, toluene, xylene, hexane, heptane, diethyl ether, tetrahydrofuran (THF), dioxane, N,N-dimethylformamide or the like, to give the compound (I) of this invention.

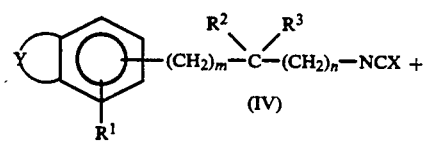
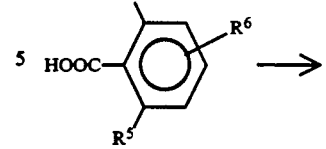

(B)

(D)

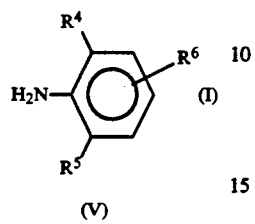

(V)

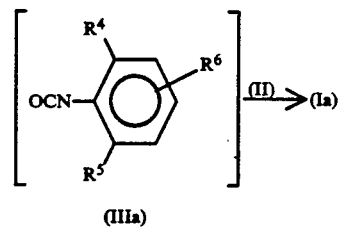

(wherein $R^1$, $R^2$, $R^3$, $R^4$, $R^5$, $R^6$, X, Y, m and n are as defined above).

A phenylalkyl isocyanate derivative (IV) (or a phenylalkyl isothiocyanate derivative) and an aniline derivative (V) are reacted under the same conditions as in the above-described process (A) to give the compound (I) of this invention.

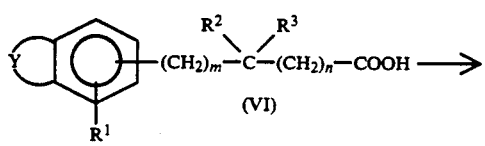

(C)

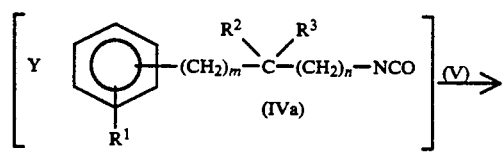

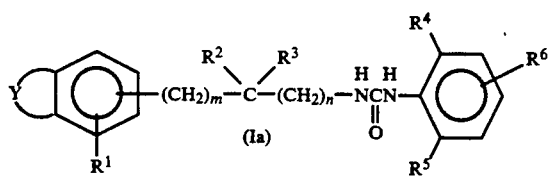

(wherein $R^1$, $R^2$, $R^3$, $R^4$, $R^5$, $R^6$, Y, m and n are as defined above).

This process is a method for synthesizing a compound of the formula (I) wherein X is oxygen. It is basically the same as the above-described process (B), but in this process, a phenylalkyl isocyanate derivative (IVa) is formed from a phenylalkylcarboxylic acid derivative (VI) and then condensed with the aniline derivative (V) to give a compound (Ia) of this invention.

As the way for converting phenylalkylcarboxylic acid derivative (VI) into phenylalkyl isocyanate derivative (IVa), there is available, for example, a method in which the reaction is carried out at a temperature in the range from room temperature to 150° C. in an inert solvent such as benzene, toluene, xylene, etc., in the presence of an organic amine which does not participate in the reaction such as triethylamine, and diphenylphosphoryl azide (DPPA). The phenylalkyl isocyanate derivative (IVa) is reacted with the aniline derivative (V) under the same conditions as in the process (B) to give the compound (Ia) of this invention.

(wherein $R^4$, $R^5$ and $R^6$ are as defined above).

This process is also a method for synthesizing a compound of the formula (I) wherein X is oxygen. In this process, a benzoic acid derivative (VII) is converted into a phenyl isocyanate derivative (IIIa) in the same way as in the process (C) and the derivative (IIIa) is condensed with a phenylalkylamine derivative (II) under the same conditions as in the process (A) to obtain the compound (Ia) of this invention.

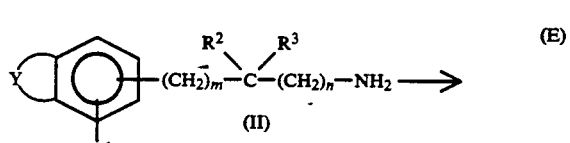

(E)

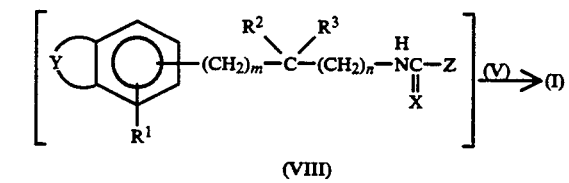

(wherein $R^1$, $R^2$, $R^3$, $R^4$, $R^5$, $R^6$, X, Y, m and n are as defined above, and Z represents an elimination group such as halo, aryloxy, alkylthio, etc.).

A phenylalkyl derivative (II) is converted into a reactive intermediate (VIII) and reacted with an aniline derivative (V) to obtain the compound (I) of this invention. As the reactive intermediate (VIII), in the case where X in the formula is oxygen, there can be mentioned a phenylalkylcarbamoyl chloride (Z in the formula (VIII) is chlorine) obtained by reacting a phenylalkylamine derivative (II) with phosgene, and an aryl phenylalkylcarbamate (Z in the formula (vIII) is aryloxy) obtained by reacting a phenylalkylamine derivative (II) with aryl chloroformate.

In the reaction for obtaining the compound of the formula (VIII) wherein X is oxygen atom, any solvent which is inactive to the reaction may be used, and for example, benzene, toluene, hexane, heptane, diethyl ether, tetrahydrofuran, dioxane and ethyl acetate may be used. Further, the reaction may be carried out preferably in the presence of an organic amine inactive to the reaction such as triethylamine and pyridine or an inorganic base such as sodium hydrogencarbonate and potassium carbonate. The reaction temperature is −15° to 100° C., preferably 0° to 50° C. The compound (vIII) thus obtained is reacted with the aniline derivative (V) to form the compound (I) of the present invention in the same reaction conditions as in the reaction of the phenylalkyl derivative (II) to the reactive intermediate (VIII).

In the case where X in the formula (VIII) is sulfur, an alkylthio ester of phenylalkylthiocarbamic acid (Z in the formula (VIII) is alkylthio group) can be mentioned as the reactive intermediate (VIII).

The alkylthio ester of phenylalkylthiocarbamic acid of the formula (vIII) wherein X is sulfur atom may be obtained by a reaction of the phenylalkyl derivative (II) with carbondisulfide and an alkyl halide in the presence of an organic amine such as triethylamine or an inorganic base such as sodium hydroxide and potassium carbonate. As the reaction solvent, any solvent which is inactive to the reaction may be used, and preferably, benzene, toluene, hexane, heptane, tetrahydrofuran, ethyl acetate and ethanol may be used. The reaction temperature is −15° to 100° C., preferably 0° to 50° C. The thus obtained alkylthio ester is converted into the compound (I) of the present invention in the same manner as in the reaction of the phenylalkyl derivative (II) to the reactive intermediate (VIII) wherein X is oxygen atom described above.

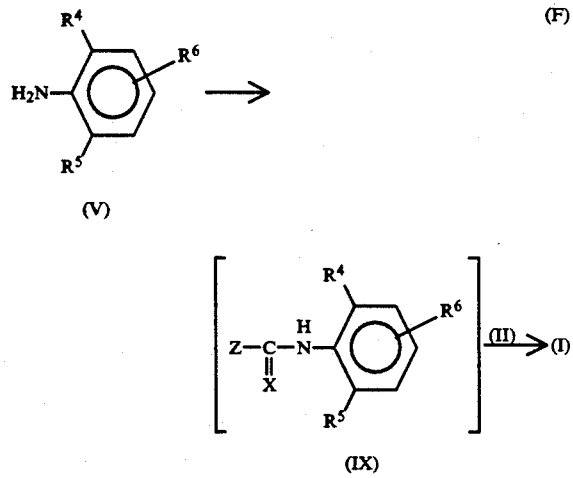

(wherein $R^4$, $R^5$, $R^6$, X and Z are as defined above).

This process is a method for obtaining a compound (I) of this invention by converting an aniline derivative (V) into a reactive intermediate (IX) and then reacting with a phenylalkylamine derivative (II).

As the reactive intermediate (IX), in the case where X in the formula (IX) is oxygen, there can be mentioned a phenylcarbamoyl chloride (Z in the formula (IX) is chlorine) obtained by reacting an aniline derivative (V) with phosgene, and an aryl phenylcarbamate (Z in the formula (IX) is aryloxy) obtained by reacting an aniline derivative (V) with aryl chloroformate. In the case where X in the formula (IX) is sulfur, an alkylthio ester of a phenylthiocarbamic acid (Z in the formula (IX) is alkylthio) can be mentioned as the reactive intermediate (IX).

The reaction conditions for obtaining the reactive intermediate (IX) and converting the reactive intermediate (IX) into the compound (I) of the present invention are the same as described in the reaction scheme (E).

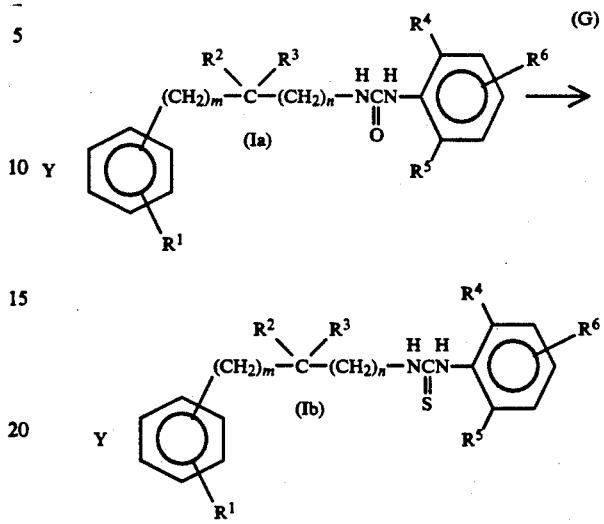

(wherein $R^1$, $R^2$, $R^3$, $R^4$, $R^5$, $R^6$, Y, m and n are as defined above).

This process is a method for synthesizing a compound (Ib) of this invention represented by the formula (I) wherein X is sulfur. This is a method for converting a urea derivative to a thiourea derivative in which a compound (Ia) of this invention (X=oxygen) is converted into a compound (Ib) by way of a Lawsson's reagent, phosphorous pentasulfide, etc. As the reaction solvent, any solvent which is inactive to the reaction may be used, and preferably, benzene, toluene, hexane, heptane, pyridine, and tetrahydrofuran may be used. The reaction temperature is 0° to 150° C., preferably 20° to 100° C.

In the above processes (A) to (F), the starting substances, the phenyl isocyanate derivative (or the phenyl isothiocyanate derivative) (III), aniline derivative (V) and benzoic acid derivative (VII), are known or can be obtained by a known method.

The processes for producing the starting substances, the phenylalkylamine derivative (II), phenylalkyl isocyanate derivative (or phenylalkyl isothiocyanate derivative) (IV) and phenylalkylcarboxylic acid derivative (VI), the processes are different where n is 0 and where n is an integer from 1 to 3.

When n is 0, each of the starting substances (II), (IV) and (VI) may be obtained as follows.

The phenylalkylcarboxylic acid derivative (VI) can be produced by, for example, methods similar to the various methods described in J-P. Pieu, Tetrahedron, (1985), 4095. The phenylalkylamine derivative (II) can be produced from the phenylalkylcarboxylic acid derivative (VI) by, for example, a method through Hofmann rearrangement, Schmidt rearrangement or Curtius rearrangement, described in E.S. Wallis, J.F. Lano, Organic Reactions 3, 267 (1946), H. Wolff, Organic Reactions 3, 307 (1946), P.A.S. Smith, Organic Reactions 3,337 (1946). The phenylalkyl isocyanate (IV) can be obtained from the phenylalkylamine derivative (II) by, for example, a method similar to the method described in Shin-Jikken Kagaku Koza 14, Synthesis and Reaction of Organic Compound (III), edited by Chemical Society of Japan, Maruzen 1978, p1490, p1503 (Scheme 1).

Scheme 1

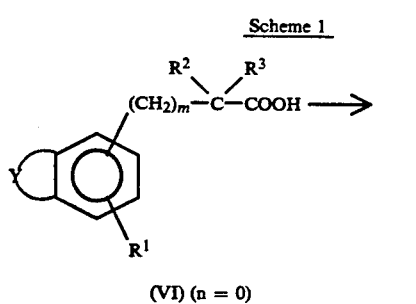

(VI) (n = 0)

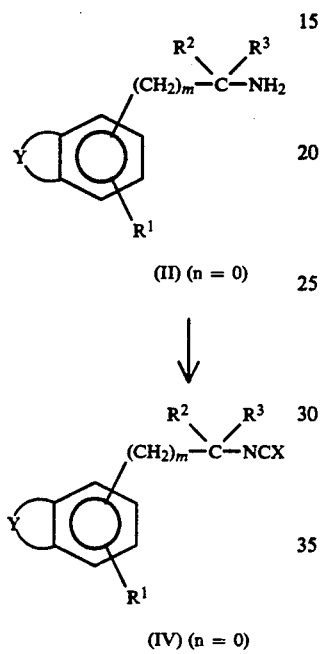

Each of the phenylalkylamine derivative (II), phenylalkyl isocyanate (or phenylalkyl isothiocyanate) (IV) and phenylalkylcarboxylic acid derivative (VI) wherein n is an integer from 1 to 3 can be produced from the phenylalkylcarboxylic acid derivative (VI) wherein n is 0 by a method for increasing the carbon number by 1 to 3. Such a method is described in Shin-Jikken Kagaku Koza 14, Synthesis and Reaction of Organic Compound (II), edited by Chemical Society of Japan, Maruzen (1978), p921 and Shin-Jikken Kagaku Koza 14, Synthesis and Reaction of Organic Compound (III), edited by Chemical Society of Japan, Maruzen (1978), p1332, p1490, p1503. For example, a phenylalkylamine derivative (II) wherein n is 1 can be produced by reacting the phenylalkylcarboxylic acid derivative (VI) wherein n is 0 with thionyl chloride to form an acid chloride (X), reacting the acid chloride (X) with ammonia to form a phenylalkylcarboxylic amide (XI), and then reducing the amide (XI) with lithium aluminum hydride (Scheme 2).

Scheme 2

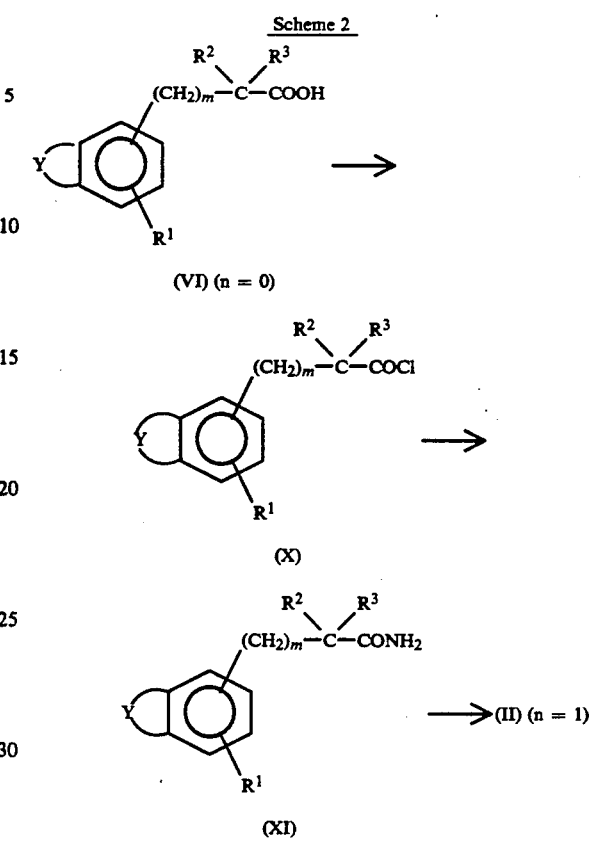

The phenylalkylamine derivative (II) wherein n is 1 can be also produced by subjecting a phenylalkylcarbonitrile (XII) to alkylation at α-carbon with respect to the cyano group to form an α-alkyl substituted phenylalkylcarbonitrile (XIII) in accordance with the method described in Shin-Jikken Kagaku Koza 14, Synthesis and Reaction of Organic Compound (III), edited by Chemical Society of Japan, Maruzen (1978), p1447, and then reducing the carbonitrile (XIII) with a reducing agent such as lithium aluminum hydride (Scheme 3).

Scheme 3

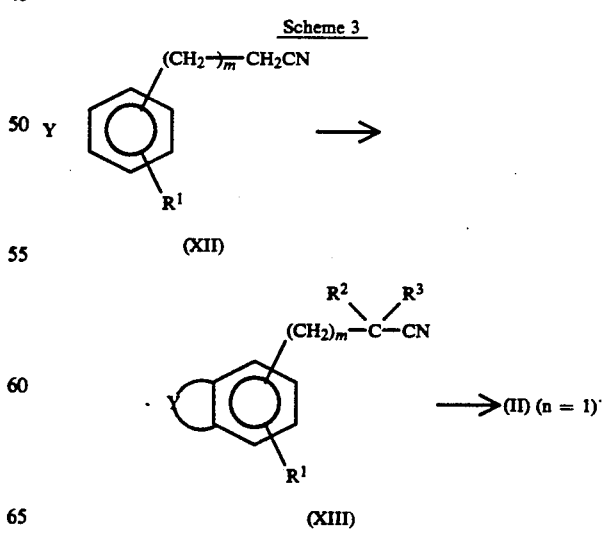

The compounds of this invention are administered to a patient preferably orally as a therapeutic agent for hyperlipemia and atherosclerosis. The formulations for oral administration can be applied in various forms such as tablet, granules, powder, capsule, etc. These formulations can be obtained by adding ordinary adjuvants, for example, excipient such as glucose, lactose, corn starch and mannitol, binder such as hydroxypropyl cellulose (HPC) and carboxymethyl cellulose (CMC), disintegrator such as starch and gelatin powder, lubricant such as talc and magnesium stearate, etc., to the compounds of this invention.

The dosage of the compounds of this invention is about 0.1 to 300 mg a day for adults in the case of oral administration. However the dosage is subject to change according to the necessity for the patient, degree of the disease to be treated and activity of the compound used.

The present invention will hereinafter be described more particularly with reference to the examples thereof. It is to be understood, however, that these examples are merely intended to be illustrative and not to be construed as limiting the scope of the invention.

REFERENCE EXAMPLE

Synthesis of 2-(2,3-methylenedioxyphenyl) heptylamine

Into 5 ml of dimethylsulfoxide, was added 0.26 g (1.6 mmol) of 2,3-methylenedioxyphenylacetonitrile, then, 0.24 g (1.6 mmol) of n-pentyl bromide and a 50% aqueous solution of sodium hydroxide were added dropwise thereinto simultaneously under cooling with ice. After 30-minute stirring at room temperature, the mixutre was added with water and extracted with ether. The ether extract was dried over magnesium chloride and then the solvent was evaporated off to obtain 0.30 g of oily 1-(2,3-methylenedioxyphenyl)hexane carbonitrile.

Then, 10 ml of ether was added to 0.06 g of lithium aluminum hydride followed by adding dropwise a solution of 0.30 g 1-(2,3-methyleneoxyphenyl)hexane carbonitrile in 5 ml ether under cooling with ice water. After 2-hour stirring at room temperature, the mixture was added with 1.6 ml of water, 1.6 ml of 15% aqueous solution of sodium hydroxide and then 4.8 ml of water. The precipitates formed were removed by filtration and the filtrate was evaporated to obtain 0.29 g of oily 2-(2,3-methylenedioxyphenyl)heptylamine (yield: 77%).

NMR (CDCL$_3$) δ: 0.84 (t, 3H), 1.19–1.25 (m, 6H), 1.56 (b.s, 2H), 2.71–2.82 (m, 1H), 2.89 (d, 2H), 5.90 (s. 2H), 6.64–6.72 (m, 2H), 6.80 (t, 1H).

EXAMPLE 1

Synthesis of 1-(2-(2,3-methylenedioxyphenyl)heptyl)-3-(2,6-diisopropylphenyl)urea Into 10 ml of ethyl ether, was added 0.29 g (1.2 mmol) of 2-(2,3-methylenedioxyphenyl)heptylamine, followed by further addition of 2.5 ml of a hexane solution (0.48 mol/l) of 2,6-diisopropylphenyl isocyanate and overnight stirring of the mixture at room temperature.

The precipitated crystals were filtered out to obtain 0.15 g of 1-(2-(2,3-methylenedioxyphenyl)heptyl)-3-(2,6-diisopropylphenyl)urea (yield: 29%). M.p.: 161°–163° C. (recrystallizing solvent: ethyl acetate/hexane).

IR (KBr) cm$^{-1}$: 3320, 2930, 1630, 1565, 1455, 1245, 1050, 725.

NMR (CDCl$_3$) δ: 0.82 (t, 3H), 1.01–1.19 (m, 18H), 1.60 (m, 2H), 2.79 (m, 1H), 3.17–3.32 (m, 3H), 3.49–3.58 (m, 1H), 4.21 (c, 1H), 5.58–5.64 (m, 3H), 6.47 (d, 2H), 6.59–6.69 (m, 2H), 7.12 (d, 2H), 7.30 (t, 1H).

EXAMPLES 2 TO 26

The compounds shown in Table 1 and Table 2 were synthesized by following the same procedure as Example 1 except for use of various kinds of phenylalkylamines in place of 2-(2,3-methylenedioxyphenyl)heptylamine.

TABLE 1

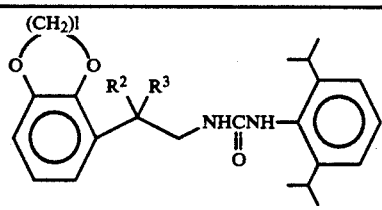

| Exam. No. | l | R$^2$ | R$^3$ | Yield (%) | M.P. (°C.) | IR (KBr) cm$^{-1}$ | NMR (CDCl$_3$)δ |
|---|---|---|---|---|---|---|---|
| 2 | 1 | H | CH$_3$ | 27 | 177–181 | 3220, 2980, 1640, 1550, 1450, 1250, 1050, 940, 810, 770, 730 | 1.11 (d, 12H), 1.26 (s, 3H), 2.99 (m, 1H), 3.19 (m, 2H), 3.25 (m, 1H), 3.49 (m, 1H), 4.28 (bs, 1H), 5.65 (m, 3H), 6.52 (m, 1H), 6.63 (m, 2H), 7.16 (d, 2H), 7.27 (t, 1H) |
| 3 | 1 | H | C$_2$H$_5$ | 34 | 150–152 | 3270, 2960, 1640, 1560, 1450, 1250, 1050, 940, 800, 700, 730 | 0.80 (t, 3H), 1.11 (d, 12H), 15.7 (m, 2H), 2.71 (m, 1H), 3.17 (bs, 2H), 3.27 (m, 1H), 3.52 (m, 1H), 4.15 (bs, 1H), 5.61 (d, 2H), 5.70 (s, 1H), 6.47 (m, 1H), 6.63 (m, 2H), 7.15 (d, 2H), 7.30 (t, 1H) |
| 4 | 1 | H | C$_3$H$_7$ (i) | 17 | 123–125 | 3300, 2920, 1640, 1550, 1450, 1240, 1050, 930, 800, 760, 730 | 0.70 (d, 3H), 0.89 (d, 3H), 1.06 (d, 12H), 1.89 (m, 1H), 2.50 (m, 1H), 3.13 (bs, 2H), 3.36 (m, 1H), 3.68 (m, 1H), 4.10 (bs, 1H), 5.59 (m, 3H), 6.40 (m, 1H), 6.57 (m, 2H), 7.09 (d, 1H), 7.27 (t, 1H) |
| 5 | 1 | H | C$_3$H$_7$ (n) | 26 | 144–146 | 3280, 2960, 1640, 1560, 1450, 1250, 1050, 940, 800, 770, 730 | 0.83 (t, 3H), 1.15 (m, 14H), 1.55 (m, 2H), 2.82 (m, 1H), 3.17 (bs, 2H), 3.27 (m, 1H), 3.53 (m, 1H), 4.22 (bs, 1H), 5.61 (d, 2H), 5.71 (s, 1H), 6.49 (m, 1H), 6.63 (m, 2H), 7.12 (d, 2H), 7.30 (t, 1H) |
| 6 | 1 | H | C$_4$H$_9$ (n) | 25 | 153–155 | 3310, 2950, 1635, 1550, 1450, 1245, 1055, 720 | 0.81 (m, 3H), 1.09–1.27 (m, 16H), 1.60 (m, 2H), 2.79 (m, 1H), 3.17–3.29 (m, 3H), 3.53 (m, 1H), 4.21 (bs, 1H), 5.61–5.67 (m, 3H), 6.46 (m, 1H), |

TABLE 1-continued

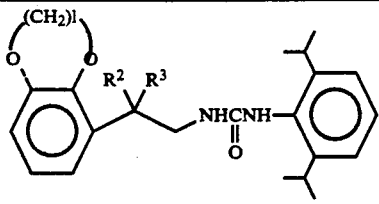

| Exam. No. | l | R² | R³ | Yield (%) | M.P. (°C.) | IR (KBr) cm⁻¹ | NMR (CDCl₃)δ |
|---|---|---|---|---|---|---|---|
| 7 | 1 | H | C₆H₁₃ (i) | 22 | 168–169 | 3320, 2960, 1635, 1555, 1450, 1245, 1055, 770, 730 | 6.62 (m, 2H), 7.15 (d, 2H), 7.30 (t, 1H) 0.78 (m, 6H), 1.01–1.21 (m, 14H), 1.43 (m, 1H), 15.7 (m, 2H), 2.79 (m, 1H), 3.18–3.31 (m, 3H), 3.52 (m, 1H), 4.20 (brs), 5.61 (s, 1H) 5.64 (s, 1H), 5.72 (s, 1H), 6.46 (m, 1H), 6.58–6.69 (m, 2H), 7.4 (d, 2H), 7.30 (t, 1H) |
| 8 | 1 | H | C₆H₁₃ (n) | 34 | 138–140 | 3300, 2930, 1650, 1550, 1450, 1250, 1050, 800, 765, 730 | 0.83 (t, 3H), 1.11 (d, 12H), 1.25 (m, 8H), 1.59 (m, 2H), 2.80 (m, 1H), 3.17 (bs, 2H), 3.28 (m, 1H), 3.54 (m, 1H), 4.21 (bs, 1H), 5.61 (d, 2H), 5.64 (s, 1H), 6.46 (m, 1H), 6.63 (m, 2H), 7.12 (d, 2H), 7.30 (t, 1H) |
| 9 | 1 | H | C₇H₁₅ (n) | 40 | 117–118 | 3300, 2910, 1640, 1550, 1450, 1250, 1050, 930, 800, 760, 730 | 0.85 (t, 3H), 1.09 (d, 12H), 1.20 (m, 10H), 1.56 (m, 2H), 2.79 (m, 1H), 3.17 (bs, 2H), 3.27 (m, 1H), 3.53 (m, 1H), 4.20 (bs, 1H), 5.61 (s, 1H), 5.64 (s, 2H), 6.46 (m, 1H), 6.61 (m, 2H), 7.12 (d, 2H), 7.30 (t, 1H) |
| 10 | 1 | H | C₉H₁₉ (n) | 33 | 94–97 | 3300, 2980, 1650, 1550, 1450, 1250, 1050, 970, 800, 770, 730 | 0.84 (t, 3H), 1.11 (d, 12H), 1.19 (m, 14H), 1.61 (m, 2H), 2.79 (m, 1H), 3.23 (m, 3H), 3.53 (m, 1H), 4.21 (bs, 1H), 5.58 (d, 2H), 5.64 (s, 1H), 6.46 (m, 1H), 6.63 (m, 2H), 7.12 (d, 1H), 7.30 (t, 1H) |
| 11 | 1 | C₂H₅ | C₂H₅ | 40 | 107–110 | 3300, 2950, 1630, 1550, 1440, 1240, 1060, 950, 760, 720 | 0.70 (t, 6H), 1.09 (d, 12H), 1.66 (m, 4H), 3.16 (m, 2H), 3.50 (m, 2H), 4.00 (t, 1H), 5.63 (d, 3H), 6.65 (m, 1H), 6.61 (m, 2H), 7.08 (d, 2H), 7.27 (t, 1H) |
| 12 | 1 | (CH₂)₄ | (CH₂)₄ | 60 | 159–160 | 3420, 2970, 1660, 1520, 1450, 1320, 1250, 1060, 940, 800, 770, 730 | 1.07 (d, 12H), 1.79 (m, 8H), 3.14 (m, 2H), 3.32 (d, 2H), 5.56 (s, 2H), 5.69 (s, 1H), 6.39 (m, 1H), 6.57 (m, 2H), 7.10 (d, 2H), 7.29 (t, 3H) |
| 13 | 1 | (CH₂)₅ | (CH₂)₅ | 63 | 142–145 | 3300, 2930, 1660, 1520, 1440, 1250, 1060, 940, 760, 730 | 1.06 (d, 12H), 1.35 (m, 8H), 2.06 (m, 2H), 3.15 (m, 2H), 3.37 (d, 2H), 4.00 (bs, 1H), 5.57 (s, 1H), 5.59 (s, 2H), 6.45 (m, 1H), 5.59 (m, 2H), 7.10 (m, 2H), 7.28 (t, 1H) |
| 14 | 2 | H | C₄H₉ (n) | 78 | 125–130 | 3400, 3310, 2940, 2870, 1640, 1500, 1470, 1280, 1255 | 0.81 (m, 3H), 1.12 (m, 16H), 1.55 (m, 2H), 3.03 (m, 1H), 3.23 (m, 2H), 3.50 (m, 1H)), 3.83 (m, 1H), 4.04 (m, 3H), 4.18 (bs, 1H), 5.56 (s, 1H), 6.52 (m, 1H), 6.63 (m, 2H), 7.13 (d, 2H), 7.27 (t, 1H) |

TABLE 2

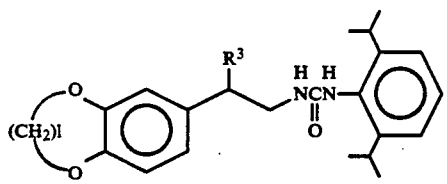

| Exam. No. | l | R³ | Yield (%) | M.P. (°C.) | IR (KBr) cm⁻¹ | NMR (CDCl₃)δ |
|---|---|---|---|---|---|---|
| 15 | 1 | C₂H₅ | 31 | 159–160 | 3330, 2960, 1630, 1565, 1485, 1245, 1035, 935, 800 | 0.76 (t, 3H), 1.10 (m, 12H), 1.43 (m, 1H), 1.63 (m, 1H), 2.45 (m, 1H), 3.02 (m, 1H), 3.15 (bs, 2H), 3.54 (m, 1H), 3.94 (bs, 1H), 5.58 (s, 1H), 5.88 (s, 1H), 6.35 (d, 1H), 6.47 (d, 1H), 6.55 (m, 1H), 7.12 (d, 2H), 7.28 (t, 1H), |
| 16 | 1 | C₃H₇ (n) | 33 | 160–161 | 3300, 2960, 1630, 1560, 1485, 1240, 1035, 935, 800 | 0.81 (t, 3H), 1.27 (m, 14H), 1.46 (m, 2H), 2.55 (m, 1H), 3.02 (m, 1H), 3.14 (bs, 2H), 3.52 (m, 1H), 3.96 (bs, 1H), 5.66 (s, 1H), 5.88 (s, 2H), 6.33 (d, 1H), 6.47 (d, 1H), 6.57 (d, 1H), 7.10 (m, 2H), 7.28 (t, 1H) |
| 17 | 1 | C₄H₉ (n) | 30 | 180–183 | 3300, 2910, 1630, 1560, 1480, 1240, 1035, 935, 800 | 0.81 (t, 3H), 1.18 (m, 16H), 1.40 (m, 2H), 2.52 (m, 1H), 3.01 (m, 1H), 3.16 (bs, 2H), 3.55 (m, 1H), 3.96 (bs, 1H), 5.67 (s, 1H), 5.89 (s, 2H), 6.33 (d, 1H), 6.47 (s, 1H), |

TABLE 2-continued

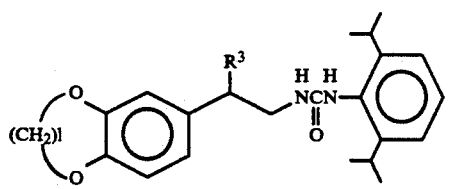

| Exam. No. | l | R³ | Yield (%) | M.P. (°C.) | IR (KBr) cm⁻¹ | NMR (CDCl₃)δ |
|---|---|---|---|---|---|---|
| 18 | 1 | $C_5H_{11}$ (n) | 36 | 174–178 | 3300, 2910, 1630, 1560, 1480, 1240, 1035, 935, 800 | 6.57 (d, 1H), 7.10 (d, 2H), 7.28 (t, 1H) 0.81 (t, 3h), 1.18 (m, 18H), 1.21 (m, 2H), 2.53 (m, 1H), 3.01 (m, 1H), 3.06 (bs, 1H), 3.52 (m, 1H), 3.94 (bs, 1H), 5.63 (s, 1H), 5.89 (s, 2H), 6.33 (d, 1H), 6.37 (d, 1H), |
| 19 | 1 | $C_6H_{13}$ (n) | 41 | 145–148 | 3300, 2910, 1630, 1560, 1485, 1240, 1035, 935, 800 | 6.54 (d, 1H), 7.13 (d, 2H), 7.28 (t, 1H) 0.83 (t, 3H), 1.13 (m, 20H), 1.45 (m, 2H), 2.54 (m, 1H), 3.02 (m, 1H), 3.16 (bs, 1H), 3.54 (m, 1H), 3.96 (bs, 1H), 5.88 (d, 3H), 6.33 (d, 1H), 6.46 (s, 1H), 6.57 (d, 1H), 7.10 (d, 2H), 7.28 (t, 1H) |
| 20 | 1 | $C_6H_{13}$ (i) | 35 | 172–174 | 3300, 2950, 1630, 1560, 1485, 1240 1040, 935, 800 | 0.79 (m, 6H), 1.13 (m, 16H), 1.45 (m, 3H), 2.53 (m, 1H), 3.01 (m, 1H), 3.15 (bs, 2H), 3.52 (m, 1H), 3.94 (bs, 1H), 5.60 (s, 1H), 5.89 (s, 2H), 6.34 (d, 1H), 6.46 (d, 1H), 6.54 (d, 1H), 7.10 (m, 2H), 7.28 (t, 1H) |
| 21 | 2 | $C_2H_5$ | 61 | 178–179 | 3320, 2960, 1635, 1560, 1510, 1285, 1255, 1070, 885 | 0.76 (t, 3H), 1.10 (m, 12H), 1.46 (m, 1H), 1.60 (m, 1H), 2.40 (m, 1H), 3.02 (m, 1H), 3.16 (bs, 2H), 3.53 (m, 1H), 3.95 (bs, 1H), 4.18 (s, 4H), 5.60 (s, 1H), 6.37 (q, 1H), 6.46 (d, 1H), 6.62 (d, 1H), 7.11 (d, 2H), 7.28 (t, 1H) |
| 22 | 2 | $C_3H_7$ (n) | 57 | 174–176 | 3340, 2960, 1630, 1565, 1505, 1285, 1250, 1070, 885 | 0.80 (t, 3H), 1.12 (m, 14H), 1.40 (m, 2H), 2.45 (m, 1H), 3.02 (m, 1H), 3.15 (bs, 2H), 3.54 (m, 1H), 3.94 (bs, 1H), 4.20 (s, 4H), 5.58 (s, 1H), 6.35 (d, 1H), 6.45 (bs, 1H), 6.60 (d, 1H), 7.12 (d, 2H), 7.26 (t, 1H) |
| 23 | 2 | $C_4H_9$ (n) | 43 | 193–194 | 3300, 2930, 1630, 1550, 1460, 1280, 1060 | 0.83 (t, 3H), 1.12 (m, 16H), 1.41 (m, 2H), 2.45 (m, 1H), 3.00 (m, 1H), 3.06 (bs, 1H), 3.51 (m, 1H), 3.95 9bs, 1H), 4.20 (s, 4H), 5.57 (s, 1H), 6.36 (d, 1H), 6.46 (d, 1H), 6.62 (d, 1H), 7.10 (d, 2H), 7.26 (t, 1H) |
| 24 | 2 | $C_5H_{11}$ (n) | 38 | 175–178 | 3300, 2930, 1630, 1560, 1280, 1070, 800 | 0.81 (t, 3H), 1.12 (m, 18H0, 1.49 (m, 2H), 2.48 (m, 1H), 3.00 (m, 1H), 3.16 (bs, 1H), 3.53 (m, 1H), 3.94 (bs, 1H), 4.20 (s, 4H) 5.58 (s, 1H), 6.35 (d, 1H), 6.45 (s, 1H), 6.62 (d, 1H, 7.10 (d, 1H), 7.28 (t, 1H) |
| 25 | 2 | $C_6H_{13}$ (n) | 31 | 147–149 | 3300, 2930, 1630, 1560, 1500, 1280, 1060, 800 | 0.82 (t, 3H), 1.10 (m, 20H), 1.46 (m, 2H), 2.48 (m, 1H), 3.00 (m, 1H), 3.16 (bs, 1H), 3.50 (m, 1H), 3.94 (bs, 1H), 4.20 (s, 4H), 5.65 (bs, 1H), 6.35 (d, 1H), 6.45 (d, 1H), 6.62 (d, 1H), 7.10 (d, 1H), 7.28 (t, 1H) |
| 26 | 3 | $C_4H_9$ (n) | 79 | 178–180 | 3340, 2970, 2940, 1635, 1568, 1505, 1300, 1258, 1050 | 0.77 (t, 3H), 1.11 (m, 12H), 1.20 (m, 4H), 1.49 (m, 2H), 2.15 (m, 2H), 2.50 (m, 1H), 3.01 (m, 1H), 3.15 (bs, 2H), 3.54 (m, 1H), 3.94 (bs, 1H), 4.14 (m, 4H), 5.54 (s, 1H), 6.45 (d, 1H), 6.75 (d, 1H), 6.71 (d, 1H), 7.10 (d, 2H), 7.26 (s, 1H) |

EXAMPLE 27

Synthesis of 1-(2-(3,4-methlenedioxybenzyl)hexyl-3-(2,6-diisopropylphenyl)urea

To 1.01 g (4.33 mmol) of 2-(3,4-methylenedioxybenzyl)hexylamine, was added 9.2 ml of a hexane solution (0.47 mmol/l) of 2,6-diisopropylphenyl isocyanate and stirred for 3 hours. The reaction solution was concentrated and then purified by silica gel column chromatography (developed with hexane/ethyl acetate=2/1) to obtain 1.13 g of 1-(2-(3,4-methylenedioxybenzyl)hexyl)-3-(2,6-diisopropylphenyl)urea as amorphous solid (yield: 60%).

IR (KBr) cm⁻¹: 3300, 2960, 1630, 1560, 1240, 1040, 930, 800

NMR (CDCl₃) δ: 0.85 (t, 3H), 1.20 (m, 18H), 1.61 (m, 1H), 2.37 (m, 2H), 3.10 (m, 2H), 3.31 (m, 2H), 4.11 (bs, 1H), 5.89 (d, 2H), 6.37 (d, 1H), 6.40 (s, 1H), 6.60 (d, 1H), 7.20 (d, 2H), 7.35 (t, 1H).

EXAMPLE 28 TO 32

The compounds shown in Table 3 were synthesized by following the same procedure as in Example 27 except for use of respective 2-(2,3-methylenedioxyphenyl)alkylamine or 2-(2,3-methylenedioxyphenylpropyl)alkylamine in place of 2-(2,3-methylenedioxybenzyl)hexylamine used in Example 27.

TABLE 3

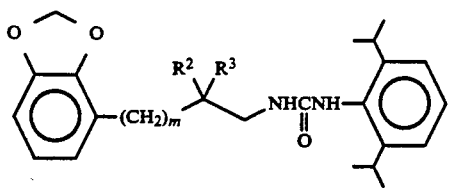

| Exam. No. | m | R² | R³ | Yield (%) | M.P. (°C.) | IR (KBr) cm⁻¹ | NMR (CDCl₃)δ |
|---|---|---|---|---|---|---|---|
| 28 | 0 | H | $C_{13}H_{27}$ (n) | 29 | 76–80 | 3300, 2910, 1650, 1550, 1450, 1250, 1060, 800, 770, 730 | 0.88 (t, 3H), 1.09 (d, 12H), 1.19 (m, 20H), 1.55 (m, 2H), 1.67 (m, 2H), 2.79 (m, 1H), 3.17 (bs, 2H), 3.28 (m, 1H), 3.53 (m, 1H), 4.21 (bs, 1H), 5.61 (2, 2H), 3.46 (m, 1H), 3.61 (m, 2H), 7.2 (d, 2H), 7.29 (t, 3H) |
| 29 | 0 | $CH_3$ | $C_5H_{11}$ (n) | 58 | 130–134 | 3300, 2910, 1630, 590, 1450, 1250, 1110, 1050, 940, 780, 725 | 0.80 (t, 3H), 1.09 (m, 18H), 1.23 (s, 3H), 1.40 (m, 1H), 1.78 (m, 1H), 3.17 (m, 2H), 3.46 (m, 2H), 4.14 (bs, 1H), 5.49 (s, 1H), 5.59 (s, 1H), 5.67 (s, 1H), 6.45 (m, 1H), 6.62 (m, 1H), 7.09 (d, 2H), 7.30 (t, 1H) |
| 30 | 0 | $C_3H_7$ (n) | $C_3H_7$ (n) | 50 | Amorphous | 3300, 2960, 1630, 1550, 1440, 1260, 1080, 950, 770, 730 | 0.79 (t, 6H), 1.10 (m, 16H), 1.54 (m, 4H), 3.17 (m, 2H), 3.50 (d, 2H), 4.07 (bs, 1H), 5.61 (s, 2H), 6.47 (m, 1H), 6.61 (m, 2H), 7.08 (d, 2H), 7.25 (t, 1H) |
| 31 | 0 | $C_5H_{11}$ (n) | $C_5H_{11}$ (n) | 48 | Oil | 3350, 2950, 1670, 1530, 1440, 1250, 1060, 960, 800, 770, 730 | 0.82 (t, 6H), 1.10 (m, 24H), 1.55 (m, 4H), 3.50 (m, 2H), 3.52 (d, 2H), 4.00 (t, 1H), 5.61 (bs, 1H), 5.64 (s, 2H), 6.60 (m, 1H), 6.61 (m, 2H), 7.09 (d, 2H), 7.27 (t, 1H) |
| 32 | 3 | H | $C_4H_9$ (n) | 44 | Oil | 3350, 2950, 1660, 1550, 1380, 1250, 1060, 940, 800, 770, 730 | 0.82 (t, 3H), 1.20 (m, 22H), 1.61 (m, 1H), 2.49 (t, 2H), 3.10 (t, 2H), 3.30 (m, 2H), 4.12 (bs, 1H), 5.88 (s, 2H), 6.61 (d, 1H), 6.69 (m, 2H), 7.18 (d, 2H), 7.21 (t, 1H) |

EXAMPLE 33

Synthesis of 1-(2-(2,3-methylenedioxyphenyl)heptyl)-3-(2,6-dimethylphenyl)urea

By following the same procedure as in Example 1 except for using 2,6-dimethylphenyl isocyanate in place of 2,6-diisopropylphenyl isocyanate, 1-(2-(2,3-methylenedioxyphenyl)heptyl)-3-(2,6-dimethylphenyl)urea was obtained (Yield: 52%).

M.p.: 131° to 134° C.

IR (KBr) cm⁻¹: 3350, 3300, 2930, 1630, 1570, 1450, 1250, 1080, 760.

NMR (CDCl₃) δ: 0.82 (t, 3H), 1.20 (m, 6H), 1.58 (m, 2H), 2.10 (s, 6H), 2.85 (m, 1H), 3.53 (m, 1H), 4.24 (t, 1H), 5.67 (d, 2H), 6.54 (m, 1H), 6.67 (m, 2H), 7.05 (m, 3H).

EXAMPLE 34

Synthesis of 1-(2-(2,3-methylenedioxyphenyl)heptyl)-3-(2,6-dichlorophenyl)urea

Into 0.92 g (3.91 mmol) of 1-(2,3-methylenedioxyphenyl)hexylamine, was added 10 ml of an ether solution of 2,6-dichlorophenyl isocyanate (0.39 mol/l) at room temperature and stirred over night. The precipitated crystals were collected by filtration and recrystalized from a mixed solvent of ethyl acetate and hexane to obtain 0.5 g of 1-(2-(2,3-methylenedioxyphenyl)heptyl)-3-(2,6-dichlorophenyl)urea (Yield: 30%).

M.p.: 164° to 166° C.

IR (KBr) cm⁻¹: 3300, 2850, 1640, 1580, 1450, 1250, 1050, 770.

NMR (CDCl₃) δ: 0.83 (t, 3H), 1.21 (m, 6H), 1.62 (m, 2H), 2.93 (m, 1H), 3.40 (m, 1H), 3.61 (m, 1H), 4.57 (t, 1H), 5,84 (S, 1H), 5.00 (bs, 1H), 6.66 (m, 3H), 7.11 (t, 1H), 7.35 (t, 3H).

EXAMPLE 35 to 41

The componds shown in Table 4 were synthesized by following the same procedure as in Example 34 except for using the corresponding substituted phenyl isocyanate in place of 2,6-dichlorophenyl isocyanate used in Example 34.

TABLE 4

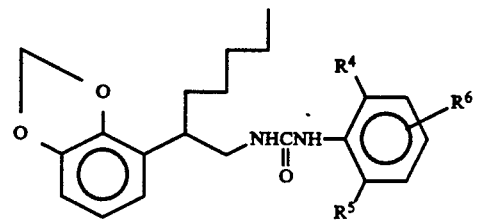

| Exam. No. | R⁴ | R⁵ | R⁶ | Yield (%) | M.P. (°C.) | IR (KBr) cm⁻¹ | NMR (CDCl₃)δ |
|---|---|---|---|---|---|---|---|
| 35 | $C_2H_5$ | $C_2H_5$ | H | 47 | Amorphous | 3300, 2950, 1630, | 0.82 (t, 3H), 1.08 (t, 6H), 1.19 (m, 6H), |

TABLE 4-continued

| Exam. No. | R⁴ | R⁵ | R⁶ | Yield (%) | M.P. (°C.) | IR (KBr) cm⁻¹ | NMR (CDCl₃)δ |
|---|---|---|---|---|---|---|---|
| | | | | | | 1550, 1440, 1240, 1060, 950, 720 | 1.54 (m, 2H), 2.46 (bs, 4H), 3.28 (m, 1H), 3.28 (m, 1H), 3.49 (m, 1H), 4.21 (t, 1H), 5.67 (bs, 3H), 6.49 (d, 1H), 6.65 (m, 2H), 7.06 (d, 2H), 7.24 (t, 1H) |
| 36 | C₂H₅ | C₄H₉ (s) | H | 58 | Amorphous | 3300, 2850, 1630, 1560, 1450, 1250, 1050, 950, 870, 730 | 0.74 (t, 3H), 0.82 (t, 3H), 1.09 (m, 6H), 1.11 (m, 6H), 1.43 (m, 4H), 2.46 (bs, 2H), 2.79 (m, 1H), 2.99 (m, 1H), 3.29 (bs, 1H), 3.49 (m, 1H), 4.19 (bs, 1H), 5.64 (m, 3H), 6.50 (d, 1H), 6.64 (m, 2H), 7.10 (t, 2H), 7.27 (t, 1H) |
| 37 | F | F | H | 17 | 129–132 | 3350, 2950, 1640, 1560, 1460, 1245, 1060, 1000, 780, 730 | 0.83 (t, 3H), 1.23 (m, 6H), 1.65 (m, 2H), 2.93 (m, 1H), 3.29 (m, 1H), 3.62 (m, 1H), 4.70 (bs, 1H), 5.83 (s, 1H), 5.86 (s, 2H), 6.61 (m, 1H), 6.67 (m, 2H), 6.87 (m, 2H), 7.14 (m, 1H) |
| 38 | Br | Br | H | 23 | 178–182 | 3310, 2950, 1640, 1580, 1450, 1250, 1060, 765, 715 | 0.85 (t, 3H), 1.22 (m, 6H), 1.64 (m, 2H), 2.93 (m, 1H), 3.36 (m, 1H), 3.59 (m, 1H), 4.58 (t, 1H), 5.83 (s, 2H), 6.06 (bs, 1H), 6.64 (m, 3H), 6.97 (t, 1H0, 7.55 (d, 2H) |
| 39 | CH₃ | CH₃ | 4CH₃ | 16 | 115–118 | 3330, 2850, 1630, 1580, 1450, 1250, 1055, 940, 850, 730 | 0.82 (t, 3H), 1.19 (m, 6H), 1.63 (m, 2H), 2.05 (s, 6H), 2.27 (s, 3H), 2.91 (m, 1H), 3.28 (m, 1H), 3.50 (m, 1H), 4.20 (t, 1H), 5.48 (bs, 1H), 5.68 (s, 2H), 6.52 (t, 1H), 6.66 (t, 2H), 6.84 (s, 2H) |
| 40 | Cl | Cl | 3-CH₃ | 21 | 176–178 | 3350, 2950, 1640, 1580, 1450, 1250, 1050, 805, 725 | 0.83 (t, 3H), 1.22 (m, 6H), 1.61 (m, 2H), 2.34 (s, 3H), 2.92 (m, 1H), 3.33 (m, 1H), 3.58 (m, 1H), 4.58 (t, 1H), 5.83 (s, 2H), 6.02 (s, 1H), 6.61 (m, 3H), 7.05 (d, 1H), 7.25 (d, 1H) |
| 41 | Cl | Cl | 4-Cl | 22 | 112–113 | 3350, 2950, 1640, 1595, 1455, 1250, 1060, 940, 875, 730 | 0.83 (t, 3H), 1.22 (m, 6H), 1.61 (m, 2H), 2.91 (m, 1H), 3.32 (m, 1H), 3.55 (m, 1H), 4.70 (bs, 1H), 5.86 (s, 2H), 6.10 (s, 1H), 6.59 (m, 1H), 6.71 (m, 2H), 7.31 (s, 2H) |

EXAMPLE 42 TO 45

The compounds shown in Table 5 were synthesized by following the same procedure as Example 34 except for use of 2-(3,4-methylenedioxyphenyl)hexylamine in place of 2-(2,3-methylenedioxyphenyl)heptylamine used in Example 34 and replacement of 2,6-diichlorophenyl isocyanate with corresponding substituted phenyl isocyanates.

TABLE 5

| Exam. No. | R⁴ | R⁵ | R⁶ | Yield (%) | M.P. (°C.) | IR (KBr) cm⁻¹ | NMR (CDCl₃)δ |
|---|---|---|---|---|---|---|---|
| 42 | CH₃ | CH₃ | 4,CH₃ | 78 | 119–122 | 3320, 2920, 1630, 1565, 1485, 1240, 1040, 935, 805 | 0.81 (t, 3H), 1.16 (m, 4H), 1.46 (m, 2H), 2.01 (s, 6H), 2.26 (s, 3H), 2.58 (m, 1H), 3.03 (m, 1H), 3.52 (m, 1H), 4.03 (bs, 1H), 5.59 (s, 1H), 5.91 (s, 2H), 5.43 (d, 1H), 6.51 (s, 1H), 6.62 (d, 1H), 6.85 (s, 1H) |
| 43 | CH₃ | C₄H₉ (t) | H | 39 | amorphous | 3300, 2920, 1630, 1560, 1490, 1240, 940, 810 | 0.80 (t, 3H), 1.23 (m, 13H), 1.52 (m, 2H), 2.10(d, 3H), 2.56 (m, 1H), 3.13 (m, 1H), 3.52 (m, 1H), 3.93 (m, 1H), 5.70 (s, 1H), 5.91 (s, 2H), 6.40 (d, 1H), 6.58 (s, 1H), 6.61 (d, 1H), 7.14 (m, 2H), 7.23 (bs, 1H) |
| 44 | C₂H₅ | C₂H₅ | H | 67 | amorphous | 3300, 2930, 1630, 1560, 1490, 1240, 1040, 940, 800 | 0.80 (t, 3H), 1.13 (m, 10H), 1.45 (m, 2H), 2.52 (m, 5H), 3.00 (m, 1H), 3.48 (m, 1H), 4.00 (bs, 1H), 5.91 (d, 3H), 6.37 (m, 1H), |

TABLE 5-continued

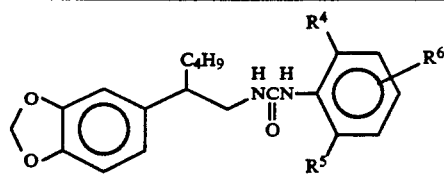

| Exam. No. | $R^4$ | $R^5$ | $R^6$ | Yield (%) | M.P. (°C.) | IR (KBr) cm$^{-1}$ | NMR (CDCl$_3$)δ |
|---|---|---|---|---|---|---|---|
| 45 | Cl | Cl | H | 58 | 134–135.5 | 3370, 2930, 1640, 1575, 1490, 1240, 1040, 940, 700 | 6.40 (d, 1H), 6.61 (d, 1H), 7.05 (d, 2H), 7.23 (t, 1H) 0.82 (t, 3H), 1.19 (m, 4H), 1.50 (m, 2H), 2.68 (m, 1H), 3.08 (m, 1H), 3.63 (m, 1H), 4.40 (bs, 1H), 5.92 (d, 2H), 6.54 (d, 1H), 6.57 (d, 1H), 6.70 (d, 1H), 7.12 (m, 1H), 7.31 (d, 2H) |

EXAMPLE 46

Synthesis of 1-(3-(2,3-methylenedioxyphenyl)octyl)-3-(2,6-diisopropylphenyl)urea The titled compound was synthesized by following the same procecure as in place of 2-(2,3-mentylenedioxyphenyl)-heptylamine used in Example 1 (Yield:88%).

M.p.: 132° to 133° C.

IR (KBr) cm$^{-1}$: 3370, 3280, 2940, 1630, 1570, 1455, 1250, 1060, 945, 730

NMR (CDCl$_3$) δ: 0,82 (t, 3H), 1.15–1.18 (brd, 18H) 1.52–1.62 (m, 3H), 1.85–1.88 (m, 1H). 2.62–2.74 (m, 2H), 3.23–3.30 (m, 3H), 4.46 (t, 1H) 5.50 (s, 1H), 5,61 (s, 1H), 6.52 (d, 1H), 6.61 (d, 1H), 6.72 (t, 1H), 7.23 (t, 2H), 7,36 (b, 1H).

EXAMPLE 47

Synthesis of 1-(2-(3,4-methylenedioxyphenyl)hexyl)-3-(2,6-dimethoxyphenyl)urea

To 1 g (6.41 mmol) of 2,6-dimethoxybenzoic acid, were added 10 ml of toluene, 1.05 ml (6.79 mmol) of triethylamine and 1.41 ml (6.54 mmol) of diphenylphosphoryl azide and stirred at 100° C. for one hour. The reaction solution was cooled to room temperature, then added with a 5 ml of toluene solution of 1.40 g (6.41 mmol) of 2-(3,4-methylenedioxyphenyl)-hexylamine and stirred overnight at room temperature. The thus treated reaction solution was purified by silica gel column chromatography (developed with a 2/1 mixture of hexane and ethyl acetate) and then recrystallized from the hexane/ethyl acetate mixed solvent to obtain 330 mg of 1-(2-(3,4-methylenedioxyphenyl)hexyl)-3-(2,6-dimethyoxyphenyl)urea (yield: 12.9%).

M.p.: 152°–153° C.

IR (KBr) cm$^{-1}$: 3300, 2930, 1640, 1560, 1490, 1250, 1140, 930

NMR (CDCl$_3$) δ: 0.82 (t, 3H), 1.14 (m, 4H), 1.26 (m, 2H), 2.64 (m, 1H), 3.11 (m, 1H), 3.57 (m, 1H). 3.63 (s, 6H), 4.85 (bs, 1H), 5.71 (bs, 1H), 5.92 (s, 2H), 6.51 (m, 3H), 6.61 (d, 1H), 6.70 (d, 1H), 7.12 (t, 1H).

EXAMPLE 48

Synthesis of 1-(2-(2,3-methylenedioxyphenyl)heptyl)-3-(2,6-dimethoxyphenyl)urea

By following the same procedure as in Example 47 except for using 2-(2,3-methylenedioxyphenyl)heptylamine in place of 2-(3,4-methylenedioxyphenyl)hexylamine used in Example 47, 1-(2-(2,3-methylenedioxyphenyl)heptyl)-3-(2,6-dimethoxyphenyl)urea was obtained in a yield of 36%.

M.p.: 120° to 123° C.

IR (KBr) cm$^{-1}$: 3320, 2950, 1630, 1560, 1450, 1250, 1050, 940, 800, 760, 730.

NMR (CDCl$_3$) δ: 0.83 (t, 3H), 1.22 (m, 6H), 1.58 (m, 2H), 2.90 (m, 1H), 3.59 (m, 1H), 3.61 (m, 1H), 3.69 (s, 6H), 5.00 (bs, 1H), 5.72 (s, 2H), 5.77 (s, 1H), 6.52 (m, 3H), 6.71 (m, 2H), 7.08 (t, 1H).

EXAMPLE 49

Synthesis of 1-(2-(2,3-methylenedioxyphenyl)heptyl)-3-(2,4,6-trimethoxyphenyl)urea To 430 mg (2.0 mmol) of 2,4,6-trimethoxybenzoic acid, were added 10 ml of toluene, 0.52 ml (3.38 mmol) of triethylamine and 0.73 ml (3.40 mmol) of diphenylphosphoryl azide, and the mixture was stirred at 100° C. for one hour. After cooling the mixture to room temperature, 5 ml of a toluene solution containing 520 mg (2.2 mmol) of 2-(2,3-methylenedioxyphenyl)heptylamine was added and the mixture was stirred at room temperature over night. The reaction mixture was subjected to purification by silica-gel column chromatography and recrystallization from a mixed solvent of hexane and ethyl acetate to obtain 360 mg of 1-(2-(2,3-methylenedioxyphenyl)heptyl)-3-(2,4,6-trimethoxyphenyl)urea (Yield: 42.1%).

M.p.: 112° to 114° C.

IR (KBr) cm$^{-1}$: 3300, 2910, 1640, 1610, 1450, 1240, 1130, 1050, 950, 800, 720.

NMR (CDCl$_3$) δ: 0.83 (t, 3H), 1.22 (m, 6H), 1.62 (m, 2H), 2.89 (m, 1H), 3.29 (m, 1H), 3.55 (m, 1H), 3.67 (s, 6H), 3.81 (s, 3H), 4.71 (bs, 1H), 5.43 (s, 1H), 5.76 (m, 2H), 6.09 (s, 2H), 6.57 (m, 1H), 6.69 (m, 2H).

EXAMPLE 50

Synthesis of 1-(2-(2,3-methylenedioxyphenylmethyl)hexyl)-3-(2,6-diisopropylphenyl)urea The titled compound was obtained by following the same procedure as in Example 27 except for using 2-(2,3-methylenedioxyphenylmethyl)-hexylamine in place of 2-(3,4-methylenedioxybenzyl)hexylamine used in Example 27.

M.p.: 120° to 122° C.

IR (KBr) cm$^{-1}$: 3310, 2950, 1620, 1550, 1450, 1250, 1050, 940, 760, 720.

NMR (CDCl$_3$) δ: 0.87 (t, 3H), 1.21 (m, 18H), 1.73 (m, 1H), 2.38 (m, 1H), 2.48 (m, 1H), 2.98 (m, 1H), 3.06 (m,

1H), 3.32 (m, 2H), 4.73 (bs, 1H), 5.45 (d, 2H), 5.76 (s, 1H), 6.49 (m, 1H), 6.66 (m, 2H), 7.21 (m, 2H), 7.36 (m, 1H).

EXAMPLE 51

Synthesis of 1-(1-(2,3-methylenedioxyphenyl)hexyl)-3-(2,6-diisopropylphenyl)urea To 800 mg (3.20 mmol) of 2-(2,3-methylenedioxyphenyl)heptanoic acid, were added 10 ml of toluene, 0.59 ml (3.84 mmol) of triethylamine and 1.0 ml (4.8 mmol) of diphenylphosphoryl azide, and the mixture was stirred at 100° C. for one hour. After cooling the mixture to room temperature, 5 ml of a toluene solution containing 570 mg (3.20 mmol) of 2,6-diisopropylaniline was added and the mixture was stirred at room temperature over night. The reaction mixture was subjected to purification by silica-gel column chromatography (eluent: hexane/ethyl acetate=5/1) and recrystallization from a mixed solvent of hexane and ethyl acetate to obtain 510 mg of 1-(1-(2,3-methylenedioxyphenyl)hexyl)-3-(2,6-diisopropylphenyl)urea (Yield: 38%).

M.p.: 173° to 176° C.

IR (KBr) cm$^{-1}$: 3300, 2980, 1640, 1550, 1450, 1250, 1060, 940, 790, 760, 720.

NMR (CDCl$_3$) δ: 0.84 (t, 3H), 1.09 (m, 18H), 1.63 (m, 2H), 3.11 (bs, 1H), 3.35 (bs, 1H), 4.93 (m, 2H), 5.55 (s, 1H), 5.74 (d, 2H), 6.68 (m, 3H), 7.20 (bs, 2H), 7.30 (m, 1H).

EXAMPLE 52

Synthesis of 1-(2-(3,4-methylenedioxy-5-methoxyphexyl)hexyl)-3-(2,6-diisopropylphenyl)urea To 1.33 g (5.34 mmol) of 2-(3,4-methylenedioxy-5-methoxyphenyl)hexylamine, was added 11.5 ml of a hexane solution (0.46 mol/l) of 2,6-diisopropylphenyl isocyanate at room temperature and stirred overnight.

The precipitated crystals were filtered out to obtain 0.30 g of 1-(2-(3,4-methylenedioxy-5-methoxyphenyl)-hexyl)-3-(2,6-diisopropylphenyl)urea (Yield: 12%).

M.p.: 151°-152.5° C. (recrystallizing solvent: ethyl acetate/hexane).

IR (KBr) cm$^{-1}$: 3300, 2930, 1640, 1550, 1450, 1260

NMR (CDCl$_3$) δ: 0.81 (t, 3H), 1.10-1.23 (m, 16H), 1.60 (m, 2H), 2.51 (m, 1H), 3.03-3.16 (m, 3H), 3.53 (m, 1H), 3.78 (s, 3H), 3.94 (bs, 1H), 5.60 (s, 1H), 5.89 (m, 2H), 6.10 (d, 1H), 6.15 (d, 1H), 7.10 (d, 2H), 7.26 (t, 1H).

EXAMPLE 53

Synthesis of 1-(2-(3,4-methylenedioxyphenyl)hexyl)-3-(2,6-diisopropylphenyl)thiourea In 10 ml of dimethylformamide, were dissolved 0.50 g (2.28 mmol) of 2-(3,4-methylenedioxyphenyl)hexylamine and 0.50 g (12.28 mmol) of 2,6-diisopropylphenyl thioisocyanate and stirred at 60° C. for 3 hours. The reaction solution was added with water, extracted with ethyl acetate, washed with water and dried over anhydrous magnesium sulfate. Then the solvent was distilled away and the residue was purified by silica gel column chromatography (developed with ¼ mixture of ethyl acetate and hexane) to obtain 560 mg of 1-(2-(3,4-methylenedioxyphenyl)hexyl)-3-(2,6-diisopropylphenyl)thiourea as amorphous solid (yield: 55.8%).

IR (KBr) cm$^{-1}$: 3360, 3170, 2960, 1540, 1510, 1270, 710

NMR (CDCl$_3$) δ: 0.83 (t, 3H), 0.89 (d, 3H), 1.11 (d, 3H), 1.15 (m, 10H), 1.49 (m, 2H), 2.55 (m, 1H), 2.92 (m, 1H), 3.06 (m, 1H), 3.25 (m, 1H), 3.98 (m, 1H), 5.04 (bs, 1H), 5.89 (s, 2H), 6.19 (d, 1H), 6.38 (d, 1H), 6.44 (d, 1H), 7.06 (d, 1H), 7.19 (d, 1H), 7.29 (d, 1H), 7.36 (t, 1H)

EXAMPLE 54

Synthesis of 1-(2-(2,3-methylenedioxyphenyl)heptyl)-3-(2,6-diisopropylphenyl)thiourea The titled compound was obtained by following the same procedure as in Example 53 except for using 2-(2,3-methylenedioxyphenyl)heptylamine in place of 2-(3,4-methylenedioxyphenyl)hexylamine used in Example 53 (Yield: 60%).

M.p.: 106° to 108° C.

IR (KBr) cm$^{-1}$: 3400, 3160, 2970, 1535, 1460, 1255, 1060, 920, 730,

NMR (CDCl$_3$) δ: 0.81 (t, 3H), 0.89 (d, 3H), 1.07-1.25 (m, 15H), 1.57 (m, 2H), 2.30-2.85 (m, 1H), 2.88-3.08 (m, 2H), 3.50-3.61 (m, 1H), 3.93-4.00 (m, 1H), 5.29 (brs, 1H), 5.56 (d, 2H), 6.38 (d, 1H), 6.55-6.64 (m, 2H), 7.10 (d, 1H), 7.16 (d, 1H), 7.25-7.37 (m, 2H).

EXAMPLE 55

Synthesis of 1-(2-(2,3-tetramethylenephenyl)hexyl)-3-(2,6-diisopropylphenyl)urea After adding 2.31 g (10 mmol) of 2-(2,3-tetramethylenephenyl)-hexylamine to 20 ml of n-hexane, a n-hexane solution (0.426 mol/1) of diisopropylphenyl isocyanate was added thereto at room temperature in an amount corresponding to 10 mmol of diisopropylphenyl isocyanate. The mixture was stirred at room temperature over night. The reaction mixture was evaporated, and the residue was subjected to purification by silica-gel column chromatography (developing solvent: n-hexane/ethyl acetate=4/1) and recrystallization from methanol to obtain 3.94 g of 1-(2-(2,3-tetramethylenephenyl)hexyl)-3-(2,6-diisopropylphenyl)urea (Yield: 90%).

M.p.: 145° to 147° C.

IR (KBr) cm$^{-1}$: 3440, 2960, 2940, 2870, 1640, 1560, 1535, 1460, 1250.

NMR (CDCl$_3$) δ: 0.80 (t, 3H), 0.92-1.25 (m, 16H), 1.41-1.59 (m, 2H), 1.62 (m, 4H), 2.43-2.70 (m, 4H), 3.39-3.49 (m, 4H), 3.45 (m, 1H), 3.98 (bs, 1H), 5.57 (s, 1H), 6.81 (q, 2H), 6.93 (q, 1H), 7.10 (q, 2H), 7.26 (q, 1H).

EXAMPLE 56 TO 60

The compounds shown in Table 6 were synthesized by following the same procedure as in Example 55 except for using the corresponding substituted phenylalkylamine in place of 2-(2,3-tetramethylenephenyl)-hexylamine used in Example 55.

TABLE 6

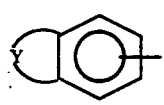

| Exam. No. |  | R² | Yield (%) | M.P. (°C.) | IR(cm⁻¹) | NMR(CDCl₃)δ |
|---|---|---|---|---|---|---|
| 56 | 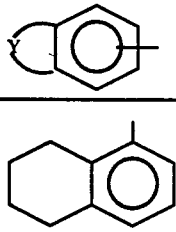 | C₅H₁₁(n) | 80 | 119–121 | 3450, 2960, 2940, 2870, 1635, 1560, 1460, 1250 | 0.81(3H, t), 0.92–1.25(18H, m), 1.52(2H, m), 1.64(4H, m), 2.49–2.70(4H, m), 3.01–3.22(4H, m), 3.44(1H, m), 3.98(1H, bs), 5.61(1H, s), 6.81(2H, q), 6.94(1H, q), 7.10(2H, d), 7.26(1H, q) |
| 57 | 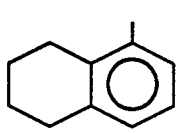 | C₆H₁₃(i) | 55 | 112–114 | 3350, 2960, 2940, 2880, 1638, 1565, 1465, 1255 | 0.77(6H, m), 0.92–1.29(17H, m), 1.49(2H, m), 1.64(4H, m), 2.49–2.77(4H, m), 3.15(4H, m), 3.44(1H, m), 3.98(1H, bs), 5.61(1H, s), 6.83(2H, q), 6.93(1H, q), 7.11(2H, d), 7.26(1H, q) |
| 58 | 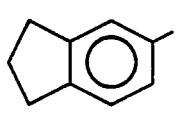 | C₅H₁₁(n) | 53 | 173–175 | 3330, 2960, 2940, 2880, 1630, 1565, 1460, 1260, 800 | 0.81(3H, t), 0.92–1.18(18H, m), 1.52(2H, m), 2.01(2H, m), 2.50(1H, m), 2.71–2.82(4H, m), 2.98–3.10(3H, m), 3.55(1H, m), 3.91(1H, brs), 5.89(1H, s), 6.66(1H, d), 6.75(1H, s), 6.95(1H, d), 7.08(2H, brs), 7.26(1H, t) |
| 59 | 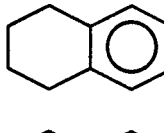 | C₅H₁₁(n) | 15 | 157–160 | 3310, 2920, 1625, 1560, 1455, 1260, 800 | 0.81(3H, c), 1.19(18H, m), 1.52(2H, m), 1.74(4H, m), 2.42(1H, m), 2.57(2H, bs), 2.66(2H, m), 3.02(1H, m), 3.10(bs, 2H), 3.58(1H, m), 3.91(1H, bs), 5.51(1H, s), 6.56(1H, s), 6.64(1H, d), 6.82(1H, d), 7.10(1H, bs), 7.26(1H, t) |
| 60 | 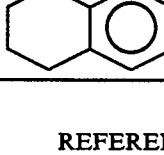 | C₅H₁₁(n) | 25 | 167–169 | 3330, 2920, 1620, 1570, 1260, 800 | 0.81(3H, t), 1.11(18H, m), 1,53(6H, m), 1.80(2H, m), 2.49(1H, m), 2.64(4H, m), 3.09(1H, m), 3.10(2H, bs), 3.55(1H, m), 3.92(bs, 1H), 5.62(1H, bs), 6.60(2H, m), 6.80(1H, d), 7.10(2H, bs), 7.26(1H, t) |

REFERENCE EXAMPLE 2

Synthesis of (-)-2-(3,4-methylenedioxyphenyl)heptanoic acid

Salt formed form 30 g (0.13 mol) of (±)-2-(3,4-methylenedioxyphenyl)heptanoic acid and R-(+)-1-phenylethylamine was recrystalized from 63% ethanol. The recrystallization was repeated once. The salt thus obtained was added with 4N hydrochloric acid and extracted with ethyl acetate. The organic layer was washed with saturated aqueous solution of sodium chloride and dried over anhydrous magnesium sulfate. By evaporating off the solvent, was obtained 6.14 g of (-)-2-(3,4-methylenedioxyphenyl)heptanoic acid (Yield: 21%). $[\alpha]_D^{21} = -40.0°$ (c=0.958, in ethanol)

REFERENCE EXAMPLE 3

Synthesis of (+)-2-(3,4-methylenedioxyphenyl)-hexylamine

To 40 ml of ether suspension containing 1.74 g (46 mmol) of lithium aluminum hydride, was added dropwise under cooling with ice 40 ml of ether solution containing 10.9 g (46 mmol) of (-)-2-(3,4-methylenedioxyphenyl)-heptanoic acid obtained in Reference Example 2. After 2-hour reflux, the reaction mixture was cooled to room temperature and was treated with water under cooling with ice to obtain 10.2 g of oily 2-(3,4-methylenedioxyphenyl)hexyl alcohol.

To 10.2 g (46 mmol) of 2-(3,4-methylenedioxyphenyl) hexyl alcohol, were added 50 ml of dichloromethane and 7.7 ml (55 mmol) of triethylamine, and further added dropwise under cooling with ice 4.3 ml (55 mmol) of mesyl chloride. After stirring for one hour at room temperature, the reaction mixture was washed with saturated aqueous sodium hydrogencarbonate and dried over anhydrous magnesium sulfate. By evaporating off the solvent, 2-(3,4-methylenedioxyphenyl)hexyl methanesulfonate was obtained in an almost quantitative yield.

To the obtained sulfonate, were added 100 ml of dimethylformamide and 8.54 g (46 mmol) of potassium phthalimide and the mixture was heated at 120° C. for 30 min. After cooled to room temperature, the reaction mixture was added with water, extracted with ethyl acetate and dried over anhydrous magnesium sulfate. The residue obtained by evaporating off the solvent was purified by silica-gel column chromatography (developing solvent: hexane/ethyl acetate=5/1) to obtain 10.7 g of N-(2-(3,4-methylenedioxyphenyl)hexyl)phthalimide (Yield: 66%).

To 10.7 g (30 mmol) of N-(2-(3,4-methylenedioxyphenyl)hexyl)-phthalimide, were added 240 ml of methanol and 3.75 ml (60 mmol) of hydrazine (mono hydrate) and the mixture was refluxed for two hours. After cooled to room temperature, the solvent was evaporated off from the reaction mixture and residue was added with 15% aqueous sodium hydroxide and extracted with ether. The organic layer was washed with saturated aqueous solution of sodium chloride and dried over anhydrous magnesium sulfate. By evaporating off the solvent, 5.0 g of oily (+)-2-(3,4-methylenedioxyphenyl)-hexylamine was obtained (Yield: 76%).
$[\alpha]_D^{21} = +2.64°$ (c=0.957, in ethanol).

NMR (CDCl$_3$) δ: 0.84 (t, 3H), 1.12 (m, 6H), 1.45 (m, 2H), 2.48 (m, 1H), 2.79 (m, 2H), 5.93 (s, 2H), 6.61 (m, 2H), 6.74 (d, 1H).

EXAMPLE 61

Synthesis of
(+)-1-(2-(3,4-methylenedioxyphenyl)-hexyl)-3-(2,6-diisopropylphenyl)urea To 4.8 g (21.7 mmol) of (+)-2-(3,4-methylenedioxyphenyl)hexylamine ($[\alpha]_D^{21} = +2.64°$, c=0.957, in ethanol), was added 46 ml of a hexane solution (0.472 M) of 2,6-diisopropylphenyl isocyanate, and the mixture was stirred for one hour at room temperature. The precipitated crystals were collected by filtration and recrystallized from ethanol to obtain 2.89 g of (+)- 1-(2-(3,4-methylenedioxyphenyl)hexyl)-3-(2,6-diisopropylphenyl)urea (Yield: 31%).

M.p.: 153° to 155° C. $[\alpha]_D^{24} = +32.4°$ (c=4.00, in methanol)

IR (KBr) cm$^{-1}$: 3330, 2950, 1630, 1570, 1480, 1240, 1040, 800.

NMR (CDCl$_3$) δ: 0.81 (t, 3H), 1.09-1.27 (m, 1H), 1.40 (m, 2H), 2.52 (m, 1H), 3.01 (m, 1H), 3.16 (bs, 2H), 3.55 (m, 1H), 3.96 (bs, 1H), 5.67 (s, 1H), 5.89 (s, 2H), 6.33 (d, 1H), 6.47 (s, 1H), 6.57 (d, 1H), 7.10 (d, 2H), 7.28 (t, 1H).

EXAMPLE 62 TO 66

The compounds shown in Table 7 were synthesized by following the same procedure as in Example 61 except for using an optically active substituted phenylalkylamine corresponding to (+)-2-(3,4-methylenedioxyphenyl)-hexylamine used in Example 61.

TABLE 7

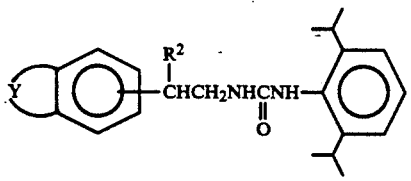

| Exam. No. | Y⟨⟩ | R² | Yield (%) | M.P. (°C.) | Optical rotation $[\alpha]_D^{24}$ | IR(KBr)cm$^{-1}$ | NMR(CDCl$_3$)δ |
|---|---|---|---|---|---|---|---|
| 62 | methylenedioxyphenyl | C$_4$H$_9$(n) | 24 | 183-184 | −39.0° c = 1.01 Methanol | 3330, 2950, 1630, 1570, 1480, 1240, 1040, 800 | 0.81(t, 3H), 1.09-1.27(m, 16H), 1.40(m, 2H), 2.52(m, 1H), 3.01(m, 1H), 3.16(bs, 2H), 3.55(m, 1H), 3.96(bs, 1H), 5.67(s, 1H), 5.89(s, 2H), 6.33(d, 1H), 6.47, S, 1H), 6.57(d, 1H), 7.10(d, 2H), 7.28(t, 1H) |
| 63 | methylenedioxyphenyl | C$_5$H$_{11}$(n) | 23 | 157-158 | +18.0° c = 1.28 Methanol | 3330, 2950, 1630, 1560, 1450, 1245, 1050, 930, 800, 760, 720 | 0.82(t, 3H), 1.01-1.09(m, 18H), 1.60(m, 2H), 2.79(m, 1H), 3.17-3.32(m, 3H), 3.49-3.58(m, 1H), 4.21(bs, 1H), 5.58-5.64(m, 3H), 6.47(d, 2H), 6.59-6.69(m, 2H), 7.12(d, 2H), 7.30(t, 1H) |
| 64 | methylenedioxyphenyl | C$_5$H$_{11}$(n) | 34 | 157-158 | −19.9° c = 1.01 Methanol | 3330, 2950, 1630, 1560, 1450, 1245, 1050, 930, 800, 760, 720 | 0.82(t, 3H), 1.01-1.09(m, 18H), 1.60(m, 2H), 2.79(m, 1H), 3.17-3.32(m, 3H), 3.49-3.58(m, 1H), 4.21(bs, 1H), 5.58-5.64(m, 3H), 6.47(d, 2H), 6.59-6.69(m, 2H), 7.12(d, 2H), 7.30(t, 1H) |
| 65 | tetrahydronaphthyl | C$_4$H$_9$(n) | 73 | 143-144 | +18.9° c=1.0 Methanol | 3360, 2970, 2940, 2870, 1630, 1570, 1460, 1250 | 0.80(t, 3H), 1.06-1.25(m, 16H), 1.44-1.74 (m, 6H), 2.49-2.70(m, 4H), 3.01-3.22(m, 4H), 3.43(m, 1H), 3.98(s, 1H), 5.58(s, 1H), 6.82 (t, 2H), 6.94(t, 1H), 7.11(d, 2H), 7.28(t, 1H) |
| 66 | tetrahydronaphthyl | C$_4$H$_9$(n) | 71 | 143-144 | −19.6° c = 1.0 Methanol | 3360, 2970, 2940, 2870, 1630, 1570, 1460, 1250 | 0.80(t, 3H), 1.06-1.25(m, 16H), 1.44-1.74 (m, 6H), 2.49-2.70(m, 4H), 3.01-3.22(m, 4H), 3.43(m, 1H), 3.98(s, 1H), 5.58(s, 1H), 6.82 (t, 2H), 6.94(t, 1H), 7.11(d, 2H), 7.28(t, 1H) |

The compounds Nos. 1 to 460 shown in Tables 8 to 19 can be also synthesized by following the same procedures as in Examples 1 to 66 described above.

The abbreviations used in Tables 8 to 19 are as follows:

| Me: | methyl | Et: | ethyl |
| n-Pr: | n-propyl | i-Pr: | isopropyl |
| n-Bu: | n-butyl | i-Bu: | isobutyl |
| n-Pe: | n-pentyl | i-Pe: | isopentyl |
| n-Hex: | n-hexyl | i-Hex: | isohexyl |
| n-Hep: | n-heptyl | i-Hep: | isoheptyl |
| n-Oct: | n-octyl | n-No: | n-nonyl |
| n-De: | n-decyl | n-Und: | n-undecyl |

-continued

| | | | |
|---|---|---|---|
| n-Dod: | n-dodecyl | n-Tri: | n-tridecyl |
| n-Tet: | n-tetradecyl | n-Ped: | n-pentadecyl |

TABLE 8

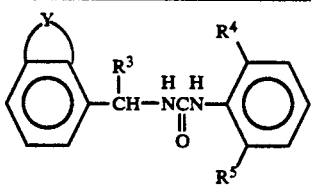

Y: —O—(CH2)l—O—

| Compound No. | l | R³ | R⁴ | R⁵ |
|---|---|---|---|---|
| 1 | 1 | Me | i-Pr | i-Pr |
| 2 | 1 | Et | i-Pr | i-Pr |
| 3 | 1 | n-Pr | i-Pr | i-Pr |
| 4 | 1 | n-Bu | i-Pr | i-Pr |
| 5 | 1 | n-Hex | i-Pr | i-Pr |
| 6 | 2 | n-Bu | Et | Et |
| 7 | 2 | n-Bu | i-Pr | i-Pr |
| 8 | 2 | n-Hep | Et | Et |
| 9 | 2 | n-Hep | i-Pr | i-Pr |

TABLE 9

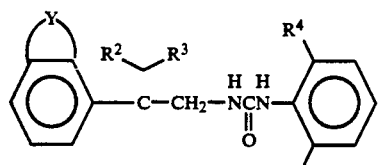

Y: —O—(CH2)l—O—

| Compound No. | l | R² | R³ | R⁴ | R⁵ |
|---|---|---|---|---|---|
| 10 | 1 | H | n-Bu | Et | Et |
| 11 | 1 | H | n-Bu | OMe | OMe |
| 12 | 1 | H | i-Pe | Et | Et |
| 13 | 1 | H | i-Pe | i-Pr | i-Pr |
| 14 | 1 | H | i-Pe | OMe | OMe |
| 15 | 1 | H | i-Pe | Cl | Cl |
| 16 | 1 | H | n-Pe | n-Pr | n-Pr |
| 17 | 1 | H | n-Pe | I | I |
| 18 | 1 | H | n-Pe | OEt | OEt |
| 19 | 1 | H | n-Pe | On-Pr | On-Pr |
| 20 | 1 | H | n-Hex | OMe | OMe |
| 21 | 1 | H | n-Hex | Cl | Cl |
| 22 | 1 | H | i-Hep | Et | Et |
| 23 | 1 | H | i-Hep | i-Pr | i-Pr |
| 24 | 1 | H | n-Hep | Et | Et |
| 25 | 1 | H | n-Oct | Et | Et |
| 26 | 1 | H | n-Oct | i-Pr | i-Pr |
| 27 | 1 | H | n-No | Et | Et |
| 28 | 1 | H | N-De | i-Pr | i-Pr |
| 29 | 1 | H | n-Und | i-Pr | i-Pr |
| 30 | 1 | H | n-Dod | i-Pr | i-Pr |
| 31 | 1 | H | n-Tri | i-Pr | i-Pr |
| 32 | 1 | H | n-Tet | i-Pr | i-Pr |
| 33 | 1 | H | N-Ped | i-Pr | i-Pr |
| 34 | 1 | Me | n-Bu | i-Pr | i-Pr |
| 35 | 1 | Me | i-Pe | i-Pr | i-Pr |
| 36 | 1 | Me | n-Hex | i-Pr | i-Pr |
| 37 | 1 | Me | i-Hex | i-Pr | i-Pr |
| 38 | 1 | Et | Et | Et | Et |
| 39 | 1 | Et | n-Pr | Et | Et |
| 40 | 1 | Et | n-Pr | i-Pr | i-Pr |
| 41 | 1 | Et | n-Bu | Et | Et |
| 42 | 1 | Et | n-Bu | i-Pr | i-Pr |
| 43 | 1 | Et | n-Pe | Et | Et |
| 44 | 1 | Et | n-Pe | i-Pr | i-Pr |
| 45 | 1 | Et | i-Pe | Et | Et |

TABLE 9-continued

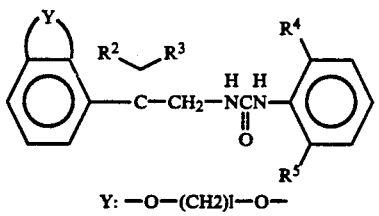

Y: —O—(CH2)l—O—

| Compound No. | l | R² | R³ | R⁴ | R⁵ |
|---|---|---|---|---|---|
| 46 | 1 | Et | i-Pe | i-Pr | i-Pr |
| 47 | 1 | Et | n-Hex | Et | Et |
| 48 | 1 | Et | n-Hex | i-Pr | i-Pr |
| 49 | 1 | Et | i-Hex | Et | Et |
| 50 | 1 | Et | i-Hex | i-Pr | i-Pr |
| 51 | 1 | n-Pr | n-Pr | Et | Et |
| 52 | 1 | n-Pr | n-Bu | Et | Et |
| 53 | 1 | n-Pr | n-Bu | i-Pr | i-Pr |
| 54 | 1 | n-Pr | n-Pe | Et | Et |
| 55 | 1 | n-Pr | n-Pe | i-Pr | i-Pr |
| 56 | 1 | n-Pr | N-Hex | i-Pr | i-Pr |
| 57 | 1 | (CH₂)₂ | (CH₂)₂ | i-Pr | i-Pr |
| 58 | 1 | (CH₂)₃ | (CH₂)₃ | i-Pr | i-Pr |
| 59 | 1 | (CH₂)₄ | (CH₂)₄ | Et | Et |
| 60 | 1 | (CH₂)₅ | (CH₂)₅ | Et | Et |
| 61 | 1 | (CH₂)₆ | (CH₂)₆ | Et | Et |
| 62 | 1 | (CH₂)₆ | (CH₂)₆ | i-Pr | i-Pr |
| 63 | 1 | (CH₂)₇ | (CH₂)₇ | i-Pr | i-Pr |
| 64 | 1 | (CH₂)₈ | (CH₂)₈ | i-Pr | i-Pr |
| 65 | 1 | (CH₂)₉ | (CH₂)₉ | i-Pr | i-Pr |
| 66 | 2 | H | n-Bu | Et | Et |
| 67 | 2 | H | n-Pe | Et | Et |
| 68 | 2 | H | n-Pe | i-Pr | i-Pr |
| 69 | 2 | H | i-Pe | Et | Et |
| 70 | 2 | H | i-Pe | i-Pr | i-Pr |
| 71 | 2 | H | n-Hex | Et | Et |
| 72 | 2 | H | n-Hex | i-Pr | i-Pr |
| 73 | 2 | H | i-Hex | Et | Et |
| 74 | 2 | H | i-Hex | i-Pr | i-Pr |
| 75 | 2 | Me | n-Bu | i-Pr | i-Pr |
| 76 | 2 | Me | n-Pe | i-Pr | i-Pr |
| 77 | 2 | Me | n-Hex | i-Pr | i-Pr |
| 78 | 2 | Et | Et | Et | Et |
| 79 | 2 | Et | Et | i-Pr | i-Pr |
| 80 | 2 | Et | n-Pr | i-Pr | i-Pr |
| 81 | 2 | Et | n-Bu | i-Pr | i-Pr |
| 82 | 2 | Et | n-Pe | i-Pr | i-Pr |
| 83 | 2 | n-Pr | n-Pr | Et | Et |
| 84 | 2 | n-Pr | n-Pr | i-Pr | i-Pr |
| 85 | 2 | n-Bu | n-Bu | i-Pr | i-Pr |
| 86 | 2 | (CH₂)₄ | (CH₂)₄ | Et | Et |
| 87 | 2 | (CH₂)₄ | (CH₂)₄ | i-Pr | i-Pr |
| 88 | 2 | (CH₂)₅ | (CH₂)₅ | Et | Et |
| 89 | 2 | (CH₂)₅ | (CH₂)₅ | i-Pr | i-Pr |
| 90 | 2 | (CH₂)₆ | (CH₂)₆ | i-Pr | i-Pr |
| 91 | 3 | H | n-Bu | i-Pr | i-Pr |
| 92 | 3 | H | n-Pe | i-Pr | i-Pr |
| 93 | 3 | H | i-Pe | i-Pr | i-Pr |
| 94 | 3 | H | n-Hex | i-Pr | i-Pr |
| 95 | 3 | H | i-Hex | i-Pr | i-Pr |
| 96 | 3 | Me | n-Pe | i-Pr | i-Pr |
| 97 | 3 | Et | Et | i-Pr | i-Pr |
| 98 | 3 | n-Pr | n-Pr | i-Pr | i-Pr |
| 99 | 3 | —(CH₂)₄— | —(CH₂)₄— | i-Pr | i-Pr |
| 100 | 3 | —(CH₂)₅— | —(CH₂)₅— | i-Pr | i-Pr |

TABLE 10

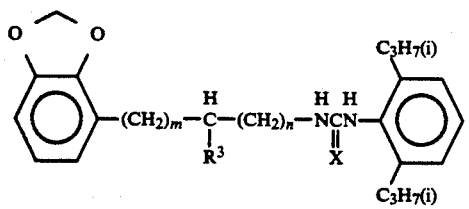

| Compound No. | R³ | m | n | x |
|---|---|---|---|---|
| 101 | n-Bu | 0 | 1 | s |
| 102 | i-Pe | 0 | 1 | s |
| 103 | n-Hex | 0 | 1 | s |
| 104 | i-Hex | 0 | 1 | s |
| 105 | n-Bu | 0 | 2 | 0 |
| 106 | n-Pe | 0 | 2 | 0 |
| 107 | n-Hex | 0 | 2 | 0 |
| 108 | i-Hex | 0 | 2 | 0 |
| 109 | n-Bu | 0 | 3 | 0 |
| 110 | n-Pe | 0 | 3 | 0 |
| 111 | n-Hex | 0 | 3 | 0 |
| 112 | n-Bu | 1 | 0 | 0 |
| 113 | n-Pe | 1 | 0 | 0 |
| 114 | n-Hex | 1 | 0 | 0 |
| 115 | n-Pe | 1 | 0 | 0 |
| 116 | n-Hex | 1 | 0 | 0 |
| 117 | n-Bu | 1 | 2 | 0 |
| 118 | n-Pe | 2 | 0 | 0 |
| 119 | n-Pe | 2 | 1 | 0 |
| 120 | n-Pe | 2 | 2 | 0 |
| 121 | n-Pe | 2 | 3 | 0 |
| 122 | n-Pe | 3 | 0 | 0 |
| 123 | n-Pe | 4 | 0 | 0 |
| 124 | n-Pe | 4 | 1 | 0 |
| 125 | n-Pe | 5 | 0 | 0 |
| 126 | n-Pe | 5 | 1 | 0 |

TABLE 11

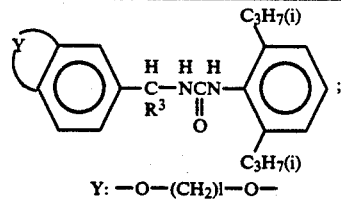

Y: —O—(CH2)l—O—

| Compound No. | l | R³ |
|---|---|---|
| 127 | 1 | Me |
| 128 | 1 | Et |
| 129 | 1 | n-Pr |
| 130 | 1 | n-Bu |
| 131 | 1 | n-Pe |
| 132 | 1 | n-Hex |
| 133 | 2 | n-Bu |
| 134 | 2 | n-Pe |

TABLE 12

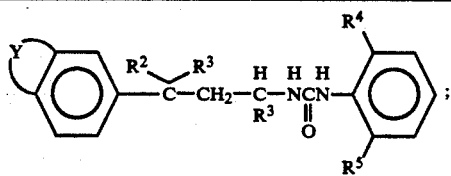

Y: —O—(CH2)l—O—

| Compound No. | l | R² | R³ | R⁴ | R⁵ |
|---|---|---|---|---|---|
| 135 | 1 | H | Me | i-Pr | i-Pr |

TABLE 12-continued

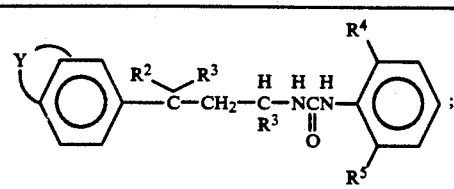

Y: —O—(CH2)l—O—

| Compound No. | l | R² | R³ | R⁴ | R⁵ |
|---|---|---|---|---|---|
| 136 | 1 | H | i-Pr | i-Pr | i-Pr |
| 137 | 1 | H | n-Bu | Me | Me |
| 138 | 1 | H | n-Bu | n-Pr | n-Pr |
| 139 | 1 | H | n-Bu | F | F |
| 140 | 1 | H | n-Bu | Br | Br |
| 141 | 1 | H | n-Bu | I | I |
| 142 | 1 | H | n-Bu | OEt | OEt |
| 143 | 1 | H | n-Bu | On-Pr | On-Pr |
| 144 | 1 | H | n-Pe | Et | Et |
| 145 | 1 | H | n-Pe | n-Pr | n-Pr |
| 146 | 1 | H | n-Pe | OMe | OMe |
| 147 | 1 | H | n-Pe | Cl | Cl |
| 148 | 1 | H | i-Pe | Et | Et |
| 149 | 1 | H | i-Pe | n-Pr | n-Pr |
| 150 | 1 | H | i-Pe | i-Pr | i-Pr |
| 151 | 1 | H | i-Pe | OMe | OMe |
| 152 | 1 | H | i-Pe | Cl | Cl |
| 153 | 1 | H | n-Hex | Et | Et |
| 154 | 1 | H | n-Hex | n-Pr | n-Pr |
| 155 | 1 | H | i-Hex | Et | Et |
| 156 | 1 | H | i-Hep | Et | Et |
| 157 | 1 | H | n-Hep | n-Pr | n-Pr |
| 158 | 1 | H | n-Hep | i-Pr | i-Pr |
| 159 | 1 | H | n-Hep | OMe | OMe |
| 160 | 1 | H | n-Hep | Cl | Cl |
| 161 | 1 | H | n-Oct | Et | Et |
| 162 | 1 | H | n-Oct | i-Pr | i-Pr |
| 163 | 1 | H | n-No | Et | Et |
| 164 | 1 | N | n-No | i-Pr | i-Pr |
| 165 | 1 | H | n-De | i-Pr | i-Pr |
| 166 | 1 | H | n-Und | i-Pr | i-Pr |
| 167 | 1 | H | n-Dod | i-Pr | i-Pr |
| 168 | 1 | H | n-Tri | i-Pr | i-Pr |
| 169 | 1 | H | n-Tet | i-Pr | i-Pr |
| 170 | 1 | H | n-Ped | i-Pr | i-Pr |
| 171 | 1 | ne | n-bu | i-Pr | i-Pr |
| 172 | 1 | ne | n-Pe | i-Pr | i-Pr |
| 173 | 1 | ne | i-Pe | i-Pr | i-Pr |
| 174 | 1 | ne | n-Hex | i-Pr | i-Pr |
| 175 | 1 | Me | i-Hex | i-Pr | i-Pr |
| 176 | 1 | EtZ | Et | Et | Et |
| 177 | 1 | Et | Et | i-Pr | i-Pr |
| 178 | 1 | Et | n-Pr | Et | Et |
| 179 | 1 | Et | n-Pr | i-Pr | i-Pr |
| 180 | 1 | Et | n-Bu | Et | Et |
| 181 | 1 | Et | n-Bu | i-Pr | i-Pr |
| 182 | 1 | Et | n-Pe | Et | Et |
| 183 | 1 | Et | n-Pe | i-Pr | i-Pr |
| 184 | 1 | Et | i-Pe | Et | ET |
| 185 | 1 | Et | i-Pe | i-Pr | i-Pr |
| 186 | 1 | Et | n-Hex | Et | EtZ |
| 187 | 1 | Et | n-Hex | i-Pr | i-Pr |
| 188 | 1 | Et | i-Hex | Et | Et |
| 189 | 1 | Et | i-Hex | i-Pr | i-Pr |
| 190 | 1 | n-Pr | n-Pr | Et | Et |
| 191 | 1 | n-Pr | n-Pr | i-Pr | i-Pr |
| 192 | 1 | n-Pr | n-Bu | Et | Et |
| 193 | 1 | n-Pr | n-Bu | i-Pr | i-Pr |
| 194 | 1 | n-Pr | n-Pe | Et | Et |
| 195 | 1 | n-Pr | n-Pe | i-Pr | i-Pr |
| 196 | 1 | n-Pr | n-Hex | i-Pr | i-Pr |
| 197 | 1 | n-Pr | i-Hex | i-Pr | i-Pr |
| 198 | 1 | —(CH2)2— | —(CH2)2— | i-Pr | i-Pr |
| 199 | 1 | —(CH2)3— | —(CH2)3— | i-Pr | i-Pr |
| 200 | 1 | —(CH2)4— | —(CH2)4— | Et | Et |
| 201 | 1 | —(CH2)4— | —(CH2)4— | i-Pr | i-Pr |
| 202 | 1 | —(CH2)5— | —(CH2)5— | Et | Et |
| 203 | 1 | —(CH2)5— | —(CH2)5— | i-Pr | i-Pr |
| 204 | 1 | —(CH2)6— | —(CH2)6— | Et | Et |

TABLE 12-continued

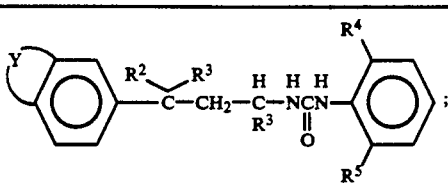

Y: —O—(CH2)l—O—

| Compound No. | l | R² | R³ | R⁴ | R⁵ |
|---|---|---|---|---|---|
| 205 | 1 | —(CH₂)₆— | —(CH₂)₆— | i-Pr | i-Pr |
| 206 | 1 | —(CH₂)₇— | —(CH₂)₇— | i-Pr | i-Pr |
| 207 | 1 | —(CH₂)₈— | —(CH₂)₈— | i-Pr | i-Pr |
| 208 | 1 | —(CH₂)₉— | —(CH₂)₉— | i-Pr | i-Pr |
| 209 | 2 | H | n-Bu | Et | Et |
| 210 | 2 | H | n-Pe | Et | Et |
| 211 | 2 | H | i-Pe | Et | ET |
| 212 | 2 | H | i-Pe | i-Pr | i-Pr |
| 213 | 2 | H | i-Hex | i-Pr | i-Pr |
| 214 | 2 | Et | n-Bu | i-Pr | i-Pr |
| 215 | 2 | Et | n-Pe | i-Pr | i-Pr |
| 216 | 2 | n-Pr | n-Pr | Et | Et |
| 217 | 2 | n-Pr | n-Pr | i-Pr | i-Pr |
| 218 | 2 | n-Bu | n-Bu | i-Pr | i-Pr |
| 219 | 2 | —(CH₂)₄— | —(CH₂)₄— | Et | Et |
| 220 | 2 | —(CH₂)₄— | —(CH₂)₄— | i-Pr | i-Pr |
| 221 | 2 | —(CH₂)₅— | —(CH₂)₅— | Et | Et |
| 222 | 2 | —(CH₂)₅— | —(CH₂)₅— | i-Pr | i-Pr |
| 223 | 2 | —(CH₂)₆— | —(CH₂)₆— | i-Pr | i-Pr |
| 224 | 3 | H | n-Pe | i-Pr | i-Pr |
| 225 | 3 | H | i-Pe | i-Pr | i-Pr |
| 226 | 3 | H | n-Hex | i-Pr | i-Pr |
| 227 | 3 | H | i-Hex | i-Pr | i-Pr |
| 228 | 3 | Me | n-Pe | i-Pr | i-Pr |
| 229 | 3 | Et | Et | i-Pr | i-Pr |
| 230 | 3 | n-Pr | n-Pr | i-Pr | i-Pr |
| 231 | 3 | —(CH₂)₄— | —(CH₂)₄— | i-Pr | i-Pr |
| 232 | 3 | —(CH₂)₅— | —(CH₂)₅— | i-Pr | i-Pr |

TABLE 13

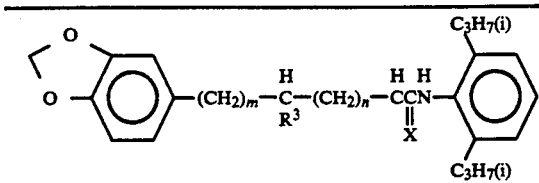

| Compound No. | R³ | m | n | x |
|---|---|---|---|---|
| 233 | n-Pe | 0 | 1 | s |
| 234 | i-Pe | 0 | 1 | s |
| 235 | n-hex | 0 | 1 | s |
| 236 | n-Pr | 0 | 2 | 0 |
| 237 | n-Bu | 0 | 2 | |
| 238 | n-Pe | 0 | 2 | |
| 239 | i-Pe | 0 | 2 | |
| 240 | n-Hex | 0 | 2 | |
| 241 | i-hex | 0 | 2 | |
| 242 | n-Bu | 0 | 3 | |
| 243 | n-Pe | 0 | 3 | |
| 244 | n-Hex | 0 | 3 | |
| 245 | n-Bu | 1 | 3 | |
| 246 | n-Pe | 1 | 3 | |
| 247 | n-Hex | 1 | 3 | |
| 248 | n-Pe | 1 | 1 | 0 |
| 249 | n-Hex | 1 | 1 | 0 |
| 250 | n-Bu | 1 | 2 | 0 |
| 251 | n-Pe | 1 | 2 | 0 |
| 252 | n-Bu | 2 | 0 | 0 |
| 253 | n-Bu | 2 | 0 | 0 |
| 254 | n-Bu | 2 | 1 | 0 |
| 255 | n-Bu | 2 | 2 | 0 |
| 256 | n-Bu | 2 | 3 | 0 |
| 257 | n-Pe | 3 | 0 | 0 |
| 258 | n-Pe | 3 | 1 | 0 |

TABLE 13-continued

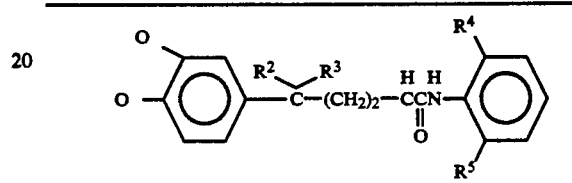

| Compound No. | R³ | m | n | x |
|---|---|---|---|---|
| 259 | n-Pe | 4 | 0 | 0 |
| 260 | n-Pe | 4 | 1 | 0 |
| 261 | n-Pe | 5 | 0 | 0 |
| 262 | n-Pe | 5 | 1 | 0 |

TABLE 14

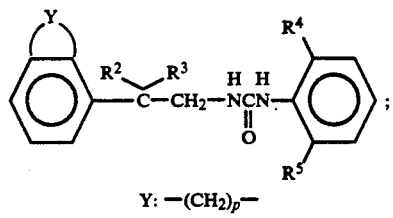

| Compound No. | R² | R³ | R⁴ | R⁵ |
|---|---|---|---|---|
| 263 | H | n-Pr | i-Pr | i-Pr |
| 264 | Me | n-Bu | i-Pr | i-Pr |
| 265 | Me | n-Pe | i-Pr | i-Pr |
| 266 | Me | n-Hex | i-Pr | i-Pr |
| 267 | Et | Et | Et | Et |
| 268 | Et | Et | i-Pr | i-Pr |
| 269 | Et | n-Pr | i-Pr | i-Pr |

TABLE 15

Y: —(CH₂)p—

| Compound No. | p | R² | R³ | R⁴ | R⁵ |
|---|---|---|---|---|---|
| 270 | 4 | H | i-Pr | i-Pr | i-Pr |
| 271 | 4 | H | n-Hex | i-Pr | i-Pr |
| 272 | 4 | H | n-Hep | i-Pr | i-Pr |
| 273 | 4 | H | n-Oct | i-Pr | i-Pr |
| 274 | 4 | H | n-Dec | i-Pr | i-Pr |
| 275 | 4 | H | n-Pr | Et | Et |
| 276 | 4 | H | n-Bu | Et | Et |
| 277 | 4 | H | n-Pe | Et | Et |
| 278 | 4 | H | n-Hex | Et | Et |
| 279 | 4 | H | i-Hex | Et | Et |
| 280 | 4 | H | n-Pr | Cl | CL |
| 281 | 4 | H | n-Bu | Cl | Cl |
| 282 | 4 | H | n-Pe | Cl | Cl |
| 283 | 4 | H | n-Hex | Cl | Cl |
| 284 | 4 | H | i-Hex | Cl | Cl |
| 285 | 4 | H | n-Pr | OMe | OMe |
| 286 | 4 | H | n-Bu | OMe | OMe |
| 287 | 4 | H | n-Pe | OMe | OMe |
| 288 | 4 | H | n-Hex | OMe | OMe |
| 289 | 4 | h | i-Hex | OMe | OMe |
| 290 | 3 | H | n-Pe | i-Pr | i-Pr |
| 291 | 3 | H | n-Hex | i-Pr | i-Pr |
| 292 | 3 | H | i-Hex | i-Pr | i-Pr |
| 293 | 3 | H | n-Hep | i-Pr | i-Pr |
| 294 | 3 | H | n-Oct | i-Pr | i-Pr |
| 295 | 3 | H | n-Dec | i-Pr | i-Pr |

TABLE 15-continued

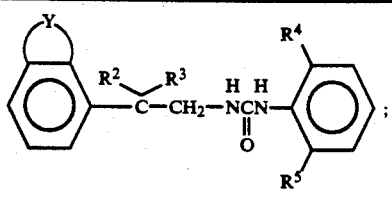

Y: —(CH$_2$)$_p$—

| Compound No. | P | R$^2$ | R$^3$ | R$^4$ | R$^5$ |
|---|---|---|---|---|---|
| 296 | 3 | H | n-Pr | Et | Et |
| 297 | 3 | H | n-Bu | Et | Et |
| 298 | 3 | H | n-Pe | Et | Et |
| 299 | 3 | H | n-Hex | Et | Et |
| 300 | 3 | H | i-Hex | Et | Et |
| 301 | 3 | H | n-Pr | Cl | Cl |
| 302 | 3 | H | n-Bu | Cl | Cl |
| 303 | 3 | H | n-Pe | Cl | Cl |
| 304 | 3 | H | n-Hex | Cl | Cl |
| 305 | 3 | H | i-Hex | Cl | Cl |
| 306 | 3 | H | n-Pr | OMe | OMe |
| 307 | 3 | H | n-Bu | OMe | OMe |
| 308 | 3 | H | n-Pe | OMe | OMe |
| 309 | 3 | H | n-Hex | OMe | OMe |
| 310 | 3 | H | i-Hex | OMe | OMe |
| 311 | 5 | H | n-Bu | i-Pr | i-Pr |
| 312 | 5 | H | n-Pe | i-Pr | i-Pr |
| 313 | 5 | H | n-Hex | i-Pr | i-Pr |
| 314 | 5 | H | i-Hex | i-Pr | i-Pr |
| 315 | 3 | Et | Et | i-Pr | i-Pr |
| 316 | 3 | n-Pr | n-Pr | i-Pr | i-Pr |
| 317 | 3 | n-Bu | n-Bu | i-Pr | i-Pr |
| 318 | 4 | Et | Et | i-Pr | i-Pr |
| 319 | 4 | n-Pr | n-Pr | i-Pr | i-Pr |
| 321 | 5 | Et | Et | i-Pr | i-Pr |
| 322 | 5 | n-Pr | n-Pr | i-Pr | i-Pr |
| 323 | 3 | —(CH$_2$)$_3$— | —(CH$_2$)$_3$— | i-Pr | i-Pr |
| 324 | 3 | —(CH$_2$)$_4$— | —(CH$_2$)$_4$— | i-Pr | i-Pr |
| 325 | 3 | —(CH$_2$)$_5$— | —(CH$_2$)$_5$— | i-Pr | i-Pr |
| 326 | 4 | —(CH$_2$)$_3$— | —(CH$_2$)$_3$— | i-Pr | i-Pr |
| 327 | 4 | —(CH$_2$)$_4$— | —(CH$_2$)$_4$— | i-Pr | i-Pr |
| 328 | 4 | —(CH$_2$)$_5$— | —(CH$_2$)$_5$— | i-Pr | i-Pr |
| 329 | 5 | —(CH$_2$)$_4$— | —(CH$_2$)$_4$— | i-Pr | i-Pr |
| 330 | 5 | —(CH$_2$)$_5$— | —(CH$_2$)$_5$— | i-Pr | i-Pr |

TABLE 16

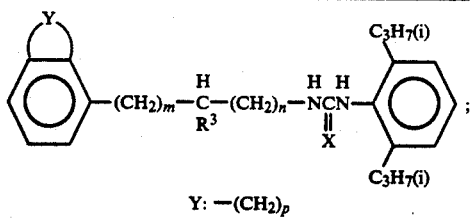

Y: —(CH$_2$)$_p$

| Compound No. | R$^3$ | P | m | n | X |
|---|---|---|---|---|---|
| 331 | n-Bu | 4 | 0 | 2 | O |
| 332 | n-Bu | 4 | 0 | 3 | O |
| 333 | n-Bu | 4 | 1 | 1 | O |
| 334 | n-Bu | 4 | 2 | 1 | O |
| 335 | n-Bu | 4 | 3 | 1 | O |
| 336 | n-Bu | 4 | 0 | 1 | S |
| 337 | n-Pr | 3 | 0 | 1 | O |
| 338 | n-Bu | 3 | 0 | 1 | O |
| 339 | n-Bu | 3 | 0 | 2 | O |
| 340 | n-Bu | 3 | 0 | 3 | O |
| 341 | n-Bu | 3 | 1 | 1 | O |
| 342 | n-Bu | 3 | 2 | 1 | O |
| 343 | n-Bu | 3 | 3 | 1 | O |
| 344 | n-Bu | 3 | 0 | 1 | S |

TABLE 17

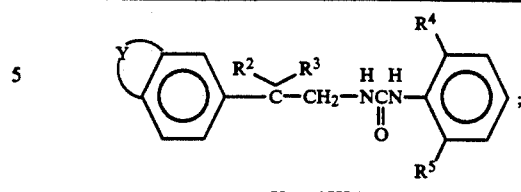

Y: —(CH$_2$)$_p$—

| Compound No. | P | R$^2$ | R$^3$ | R$^4$ | R$^5$ |
|---|---|---|---|---|---|
| 345 | 4 | H | n-Bu | i-Pr | i-Pr |
| 346 | 4 | H | n-Hex | i-Pr | i-Pr |
| 347 | 4 | H | i-Hex | i-Pr | i-Pr |
| 348 | 4 | H | n-Hep | i-Pr | i-Pr |
| 349 | 4 | H | n-Oct | i-Pr | i-Pr |
| 350 | 4 | H | n-De | i-Pr | i-Pr |
| 351 | 4 | H | n-Pr | Et | Et |
| 352 | 4 | H | n-Bu | Et | EtZ |
| 353 | 4 | H | n-Pe | Et | Et |
| 354 | 4 | H | n-Hex | Et | Et |
| 355 | 4 | H | i-Hex | Et | Et |
| 356 | 4 | H | n-Pr | Cl | Cl |
| 357 | 4 | H | n-Bu | Cl | Cl |
| 358 | 4 | H | n-Pe | Cl | Cl |
| 359 | 4 | H | n-Hex | Cl | Cl |
| 360 | 4 | H | i-Hex | Cl | Cl |
| 361 | 4 | H | n-Pr | OMe | OMe |
| 362 | 4 | H | n-Bu | OMe | OMe |
| 363 | 4 | H | n-Pe | OMe | OMe |
| 364 | 4 | H | n-Hex | OMe | OMe |
| 365 | 4 | H | i-Hex | OMe | OMe |
| 366 | 3 | H | n-Pr | i-Pr | i-Pr |
| 367 | 3 | H | n-Bu | i-Pr | i-Pr |
| 368 | 3 | H | n-Hex | i-Pr | i-Pr |
| 369 | 3 | H | i-Hex | i-Pr | i-Pr |
| 370 | 3 | H | n-Hep | i-Pr | i-Pr |
| 371 | 3 | H | n-Oct | i-Pr | i-Pr |
| 372 | 3 | H | n-De | i-Pr | i-Pr |
| 373 | 3 | H | n-Pr | Et | Et |
| 374 | 3 | H | n-Bu | Et | Et |
| 375 | 3 | H | n-Pe | Et | Et |
| 376 | 3 | H | n-Hex | Et | Et |
| 378 | 3 | H | i-Hex | Et | Et |
| 379 | 3 | H | n-Pr | Cl | Cl |
| 380 | 3 | H | n-Bu | Cl | Cl |
| 381 | 3 | H | n-Pe | Cl | Cl |
| 382 | 3 | H | n-Hex | Cl | Cl |
| 383 | 3 | H | i-Hex | Cl | Cl |
| 384 | 3 | H | n-Pr | OMe | OMe |
| 385 | 3 | H | n-Bu | OMe | OMe |
| 386 | 3 | H | n-Pe | OMe | OMe |
| 387 | 3 | H | n-Hex | OMe | OMe |
| 388 | 3 | H | i-Hex | OMe | OMe |
| 389 | 5 | H | n-Bu | i-Pr | i-Pr |
| 390 | 5 | H | n-Hex | i-Pr | i-Pr |
| 391 | 5 | H | i-Hex | i-Pr | i-Pr |
| 392 | 3 | Et | Et | i-Pr | i-Pr |
| 393 | 3 | n-Pr | n-Pr | i-Pr | i-Pr |
| 394 | 3 | n-Bu | n-Bu | i-Pr | i-Pr |
| 395 | 4 | Et | Et | i-Pr | i-Pr |
| 396 | 4 | n-Pr | n-Pr | i-Pr | i-Pr |
| 397 | 4 | n-Bu | n-Bu | i-Pr | i-Pr |
| 398 | 5 | Et | Et | i-Pr | i-Pr |
| 399 | 5 | n-Pr | n-Pr | i-Pr | i-Pr |
| 400 | 3 | —(CH$_2$)$_3$— | —(CH$_2$)$_3$— | i-Pr | i-Pr |
| 401 | 3 | —(CH$_2$)$_4$— | —(CH$_2$)$_4$— | i-Pr | i-Pr |
| 402 | 3 | —(CH$_2$)$_5$— | —(CH$_2$)$_5$— | i-Pr | i-Pr |
| 403 | 4 | —(CH$_2$)$_3$— | —(CH$_2$)$_3$— | i-Pr | i-Pr |
| 404 | 4 | —(CH$_2$)$_4$— | —(CH$_2$)$_4$— | i-Pr | i-Pr |
| 405 | 4 | —(CH$_2$)$_5$— | —(CH$_2$)$_5$— | i-Pr | i-Pr |
| 406 | 5 | —(CH$_2$)$_4$— | —(CH$_2$)$_4$— | i-Pr | i-Pr |
| 407 | 5 | —(CH$_2$)$_5$— | —(CH$_2$)$_5$— | i-Pr | i-Pr |

TABLE 18
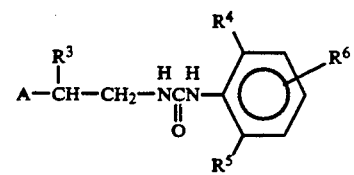
Y: —(CH$_2$)$_p$—
| Compound No. | R$^3$ | P | m | n | x |
|---|---|---|---|---|---|
| 408 | n-Bu | 3 | 0 | 2 | 0 |
| 409 | n-Bu | 3 | 1 | 1 | 0 |
| 410 | n-Bu | 3 | 2 | 1 | 0 |
| 411 | n-Bu | 4 | 0 | 2 | 0 |
| 412 | n-Bu | 4 | 1 | 1 | 0 |
| 413 | n-Bu | 4 | 2 | 1 | 0 |
| 414 | n-Bu | 4 | 3 | 1 | 0 |
| 415 | n-Bu | 4 | 0 | 1 | s |
| 416 | n-Bu | 3 | 3 | 1 | O |
| 417 | n-Bu | 3 | 3 | 1 | s |
TABLE 19
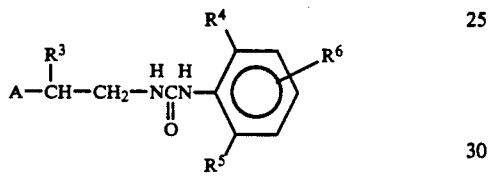
| Compound No. | A | R$^3$ | R$^4$ | R$^5$ | R$^6$ |
|---|---|---|---|---|---|
| 418 | 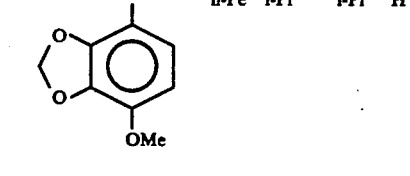 | n-Pe | i-Pr | i-Pr | H |
| 419 | | n-Bu | i-Pr | i-Pr | H |
| 420 | | n-Bu | i-Pr | i-Pr | H |
| 421 | | n-Pe | i-Pr | i-Pr | H |
| 422 | | n-Pe | i-Pr | i-Pr | H |
| 423 | | n-Pe | i-Pr | i-Pr | H |
TABLE 19-continued
| Compound No. | A | R$^3$ | R$^4$ | R$^5$ | R$^6$ |
|---|---|---|---|---|---|
| 424 | 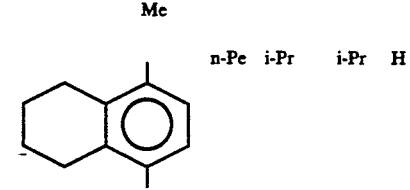 | n-Pe | i-Pr | i-Pr | H |
| 425 | 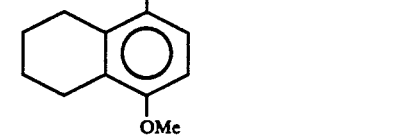 | n-Bu | i-Pr | i-Pr | H |
| 426 | 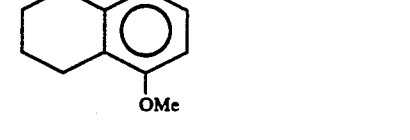 | n-Pe | i-Pr | i-Pr | H |
| 427 | 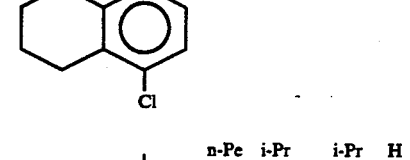 | n-Bu | i-Pr | i-Pr | H |
| 428 | | n-Pe | i-Pr | i-Pr | H |
| 429 | 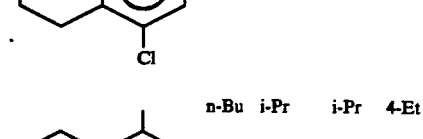 | n-Bu | i-Pr | i-Pr | H |
| 430 | | n-Pe | i-Pr | i-Pr | H |
| 431 |  | n-Bu | i-Pr | i-Pr | 4-Et |

TABLE 19-continued

Structure: A—CH(R³)—CH₂—N(H)—C(=O)—N(H)—[phenyl with R⁴ (ortho), R⁶ (para), R⁵ (other ortho)]

| Compound No. | A | R³ | R⁴ | R⁵ | R⁶ |
|---|---|---|---|---|---|
| 432 | indan-yl | n-Pe | i-Pr | i-Pr | 4-Et |
| 433 | indan-yl | n-Bu | i-Pr | i-Pr | 4-i-Pr |
| 434 | indan-yl | n-Pe | i-Pr | i-Pr | 4-i-Pr |
| 435 | indan-yl | n-Bu | i-Pr | i-Pr | 4-OMe |
| 436 | indan-yl | n-Pe | i-Pr | i-Pr | 4-OMe |
| 437 | indan-yl | n-Bu | i-Pr | i-Pr | 4-Cl |
| 438 | indan-yl | n-Pe | i-Pr | i-Pr | 4-Cl |
| 439 | indan-yl (Me) | n-Bu | i-Pr | i-Pr | H |
| 440 | indan-yl (Me) | n-Pe | i-Pr | i-Pr | H |
| 441 | indan-yl (OMe) | n-Bu | i-Pr | i-Pr | H |
| 442 | indan-yl (OMe) | n-Pe | i-Pr | i-Pr | H |
| 443 | indan-yl (Cl) | n-Bu | i-Pr | i-Pr | H |
| 444 | indan-yl (Cl) | n-Pe | i-Pr | i-Pr | H |
| 445 | tetralin-yl | n-Bu | i-Pr | i-Pr | 4-Et |
| 446 | tetralin-yl | n-Pe | i-Pr | i-Pr | 4-Et |
| 447 | tetralin-yl | n-Bu | i-Pr | i-Pr | 4-i-Pr |
| 448 | tetralin-yl | n-Pe | i-Pr | i-Pr | 4-i-Pr |
| 449 | tetralin-yl | n-Bu | i-Pr | i-Pr | 4-OMe |

TABLE 19-continued

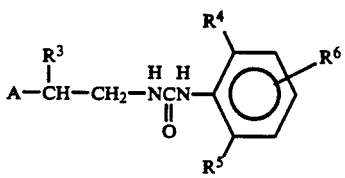

| Compound No. | A | R³ | R⁴ | R⁵ | R⁶ |
|---|---|---|---|---|---|
| 450 | 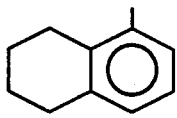 | n-Pe | i-Pr | i-Pr | 4-OMe |
| 451 | 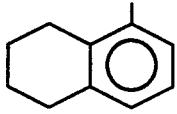 | n-Bu | i-Pr | i-Pr | 4-Cl |
| 452 | 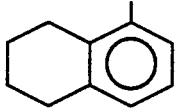 | n-Pe | i-Pr | i-Pr | 4-Cl |
| 453 | 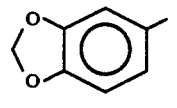 | n-Bu | OMe | OMe | 4-OMe |
| 454 | 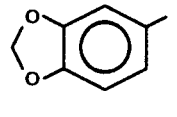 | n-Bu | Cl | Cl | 3-Me |
| 455 | 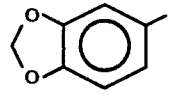 | n-Bu | Cl | Cl | 4-Cl |
| 456 | 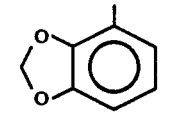 | i-Hex | Et | Et | 4-Cl |
| 457 | 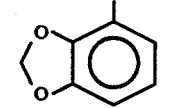 | i-Hex | OMe | OMe | 4-Cl |
| 458 | 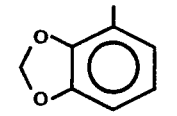 | i-Hex | Cl | Cl | 4-Cl |
| 459 | 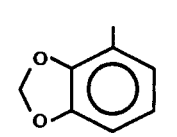 | n-Hex | Me | Me | 4-Cl |

TABLE 19-continued

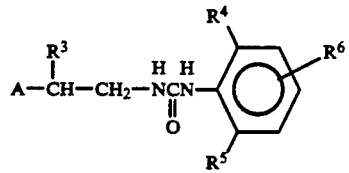

| Compound No. | A | R³ | R⁴ | R⁵ | R⁶ |
|---|---|---|---|---|---|
| 460 | 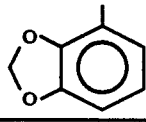 | n-Hex | Et | Et | 4-Cl |

TEST EXAMPLE 1

The effect of reducing a lipid level in blood by the action of the compounds according to the present invention was determined as follows:

Male golden hamsters weighing from 80 to 100 g were randomly divided into groups. The hamsters were first fed standard laboratory diets (solid feed MF-1 for mouse/rat/hamster, manufactured by Oriental yeast Industries, KK) for 3 days. Then, they were fed the experimental diet containing 1% cholesterol and 0.5% cholic acid ad libitum. At the same time, the compounds of the invention formulated in a shown dose (1 mg/10 ml water/kg) were administrated to the hamsters orally once a day at a determined time. Water was administrated orally to the hamsters of control group in an amount of 10 ml per 1 kg of body weight. On fifth day of administrating the compounds, the hamsters were anesthetized with nembutal (Nembutal injection, manufactured by Dainabbot) three hours after the final administration of the test compound, and a blood sample was taken from abdominal cava. The serum was separated from the sample by centrifuging.

The cholesterol level in the serum was determined by using a blood cholesterol measuring kit, Determina-TC5 manufactured by Kyowa Medix Co. The results are represented by percent inhibition (%) of cholesterol level in serum relative to that of the control group, and shown in the following Table 20.

TABLE 20

| Example No. | Reduction of Cholesterol in Blood (%) |
|---|---|
| 1 | 34 |
| 6 | 40 |
| 11 | 31 |
| 12 | 10 |
| 13 | 19 |
| 14 | 30 |
| 16 | 34 |
| 17 | 34 |
| 18 | 33 |
| 19 | 23 |
| 20 | 46 |
| 23 | 39 |
| 24 | 41 |
| 25 | 39 |
| 26 | 40 |
| 29 | 61 |
| 30 | 18 |
| 31 | 16 |
| 52 | 15 |
| 54 | 21 |
| 55 | 35 |

TABLE 20-continued

| Example No. | Reduction of Cholesterol in Blood (%) |
| --- | --- |
| 56 | 42 |
| 57 | 38 |
| 61 | 45 |
| 62 | 33 |
| 63 | 56 |
| 64 | 27 |
| 65 | 44 |
| 66 | 40 |
| Comparison[1] | 5[2] |

[1] 1-(3,3-dimethyl-2-phenylbutyl)-3-(2,6-diisopropylphenyl)urea compound disclosed in Japanese Patent Application Laid-Open (KOKAI) No. 6456/90

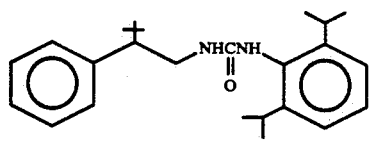

[2] Results in a dose of 5 mg/kg p.o.

TEST EXAMPLE 2

The ACAT inhibitory action of the compounds of this invention was determined by the following method.

ACAT activity was determined by measuring the amount of ratio-active cholesteryl oleate formed from radio-labelled oleoyl coenzyme A in each tissue specimen containing hamster liver microsome. The reduction rates (%) in the amount of formation of cholesteryl oleate by the administration of the test compound in various concentrations (μM) as compared with as compared with the amount of formation in the control group to which no test compound was administrated were measured. The ACAT inhibitory action was evaluated by IC50, the concentration of the test compound necessary for inhibiting the activity of the enzyme by 50%, obtained from the reduction rates. The results are shown in Table 21.

TABLE 21

| Example No. | IC$_{50}$ (μM) |
| --- | --- |
| 3 | 0.085 |
| 4 | 0.028 |
| 5 | 0.056 |
| 8 | 0.011 |
| 9 | 0.086 |
| 11 | 0.032 |
| 17 | 0.009 |
| 23 | 0.013 |
| 29 | 0.005 |
| 33 | 0.038 |
| 34 | 0.034 |
| 35 | 0.032 |
| 36 | 0.026 |
| 48 | 0.020 |
| 56 | 0.004 |
| 63 | 0.005 |
| 64 | 0.012 |
| 65 | 0.012 |
| 66 | 0.028 |

What is claimed is:

1. A 1-phenylalkyl-3-phenylurea derivative represented by the following formula (I):

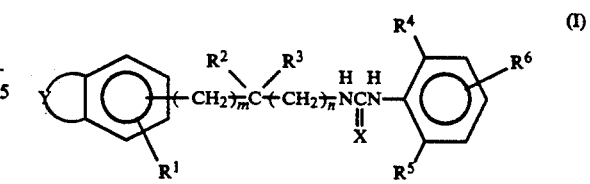

wherein $R^1$ and $R^6$ represent independently hydrogen, $C_1$–$C_{15}$ alkyl or $R^3$ represents together with $R^2$ $C_2$–$C_9$ alkylene; $R^4$ and $R^5$ represent independently $C_1$–$C_5$ alkyl, $C_1$–$C_5$ alkoxyl or halo; X represents oxygen or sulfur; Y represents —O—$(CH_2)_l$—O-13 wherein l is an integer of 1 to 3 or —$(CH_2)_p$— wherein p is an integer of 3 to 5; m is 0 or an integer of 1 to 5; and n is 0 or an integer of 1 to 3.

2. A 1-phenylalkyl-3-phenylurea derivative according to claim 1, wherein $R^2$ represents hydrogen or $C_1$–$C_5$ alkyl; $R^3$ represents $C_1$–$C_{15}$ alkyl or $R^3$ represents together with $R^2$ $C_3$–$C_5$ alkylene.

3. A 1-phenylalkyl-3-phenylurea derivative according to claim 2, wherein $R^1$ and $R^6$ represent independently hydrogen, methyl, methoxyl or chlorine.

4. A 1-phenylalkyl-3-phenylurea derivative according to claim 3, wherein m represents 0 or an integer of 1 to 3 and n represents 0, 1 or 2.

5. A 1-phenylalkyl-3-phenylurea derivative according to claim 4, wherein $R^1$ represents hydrogen.

6. A 1-phenylalkyl-3-phenylurea derivative according to claim 5, wherein $R^2$ represents hydrogen or $C_1$–$C_3$ alkyl and $R^3$ represents $C_2$–$C_8$ alkyl.

7. A 1-phenylalkyl-3-phenylurea derivative according to claim 6, wherein X represents oxygen.

8. A 1-phenylalkyl-3-phenylurea derivative according to claim 7, wherein m represents 0 and n represents 1.

9. A 1-phenylalkyl-3-phenylurea derivative according to claim 8, wherein $R^6$ represents hydrogen.

10. A 1-phenylalkyl-3-phenylurea derivative according to claim 9, wherein $R^2$ represents hydrogen and $R^3$ represents $C_4$–$C_7$ alkyl.

11. A 1-phenylalkyl-3-phenylurea derivative according to claim 10, wherein each of $R^4$ and $R^5$ represents isopropyl.

12. A 1-phenylalkyl-3-phenylurea derivative according to claim 11, wherein Y represents —O—$(CH_2)_l$—O— wherein l represents an integer of 1 to 3.

13. A 1-phenylalkyl-3-phenylurea derivative according to claim 11, wherein Y represents —$(CH_2)_p$— wherein p represents an integer of 3 to 5.

14. A 1-phenylalkyl-3-phenylurea derivative according to claim 13, wherein Y represents —$(CH_2)_4$—.

15. A acyl-CoA: cholesterol acyltransferase inhibitor comprising a 1-phenylalkyl-3-phenylurea derivative as defined in claim 1 as active ingredient.

16. A pharmaceutical composition for treating hyperlipemia and atherosclerosis comprising a therapeutically effective amount of a 1-phenylalkyl-3-phenylurea derivative according to claim 1, in admixture with a pharmaceutically acceptable carrier, diluent, or a mixture thereof.

* * * * *